US010599006B2

(12) United States Patent
Van Heugten et al.

(10) Patent No.: US 10,599,006 B2
(45) Date of Patent: Mar. 24, 2020

(54) ELECTRO-ACTIVE LENSES WITH RAISED RESISTIVE BRIDGES

(71) Applicant: e-Vision Smart Optics, Inc., Sarasota, FL (US)

(72) Inventors: Anthony Van Heugten, Sarasota, FL (US); Harry Milton, Sarasota, FL (US)

(73) Assignee: e-Vision Smart Optics, Inc., Sarasota, FL (US)

(*) Notice: Subject to any disclaimer, the term of this patent is extended or adjusted under 35 U.S.C. 154(b) by 0 days.

(21) Appl. No.: 15/431,686

(22) Filed: Feb. 13, 2017

(65) Prior Publication Data
US 2017/0293197 A1 Oct. 12, 2017

Related U.S. Application Data

(63) Continuation of application No. PCT/US2016/060784, filed on Nov. 7, 2016.
(Continued)

(51) Int. Cl.
G02F 1/29 (2006.01)
G02F 1/133 (2006.01)
A61F 2/16 (2006.01)

(52) U.S. Cl.
CPC ............ G02F 1/29 (2013.01); A61F 2/16 (2013.01); G02F 1/13306 (2013.01); G02F 2001/294 (2013.01); G02F 2201/122 (2013.01)

(58) Field of Classification Search
CPC ...................................................... A61F 2/16
See application file for complete search history.

(56) References Cited

U.S. PATENT DOCUMENTS 2,437,642 A 3/1948 Henroleau
2,576,581 A 11/1951 Edwards
(Continued)

FOREIGN PATENT DOCUMENTS

CN 89113088 10/2001
CN 101133449 A 2/2008
(Continued)

OTHER PUBLICATIONS

International Search Report and Written Opinion of the International Searching Authority in regards to International Application No. PCT/US16/60784, dated Jan. 19, 2017, 14 pages.
(Continued)

Primary Examiner — Michael H Caley
Assistant Examiner — Mariam Qureshi
(74) Attorney, Agent, or Firm — Smith Baluch LLP

(57) ABSTRACT

Resistive bridges can connect many ring electrodes in an electro-active lens with a relatively small number of buss lines. These resistors are usually large to prevent excessive current consumption. Conventionally, they are disposed in the same plane as the ring electrodes, which means that the ring electrodes are spaced farther apart or made discontinuous to accommodate the resistors. But spacing the ring electrodes farther apart or making them discontinuous degrades the lens's optical quality. Placing the ring electrodes and resistors on layers separated by an insulator makes it possible for the ring electrodes to be closer together and continuous with resistance high enough to limit current consumption. It also relaxes constraints on feature sizes and placement during the process used to make the lens. And because the resistors and electrodes are on different planes, they can be formed of materials with different resistivities.

34 Claims, 20 Drawing Sheets

Related U.S. Application Data

(60) Provisional application No. 62/321,501, filed on Apr. 12, 2016.

(56) References Cited

U.S. PATENT DOCUMENTS

| | | | |
|---|---|---|---|
| 3,161,718 | A | 12/1964 | DeLuca |
| 3,245,315 | A | 4/1966 | Marks et al. |
| 3,248,460 | A | 4/1966 | Naujokas |
| 3,309,162 | A | 3/1967 | Kosanke et al. |
| 3,614,215 | A | 10/1971 | Mackta |
| 3,738,734 | A | 6/1973 | Tait et al. |
| 3,791,719 | A | 2/1974 | Kratzer et al. |
| 4,062,629 | A | 12/1977 | Winthrop |
| 4,174,156 | A | 11/1979 | Glorieux |
| 4,181,408 | A | 1/1980 | Senders |
| 4,190,330 | A | 2/1980 | Berreman |
| 4,190,621 | A | 2/1980 | Greshes |
| 4,264,154 | A | 4/1981 | Petersen |
| 4,279,474 | A | 7/1981 | Belgorod |
| 4,300,818 | A | 11/1981 | Schachar |
| 4,320,939 | A | 3/1982 | Mueller |
| 4,373,218 | A | 2/1983 | Schachar |
| 4,395,736 | A | 7/1983 | Fraleux |
| 4,418,990 | A | 12/1983 | Gerber |
| 4,423,929 | A | 1/1984 | Gomi |
| 4,457,585 | A | 7/1984 | DuCorday |
| 4,461,550 | A | 7/1984 | Legendere |
| 4,466,703 | A | 8/1984 | Nishimoto |
| 4,466,706 | A | 8/1984 | Lamothe, II |
| 4,529,268 | A | 7/1985 | Brown |
| 4,564,267 | A | 1/1986 | Nishimoto |
| 4,572,616 | A | 2/1986 | Kowel et al. |
| 4,577,928 | A | 3/1986 | Brown |
| 4,601,545 | A | 7/1986 | Kern |
| 4,609,824 | A | 9/1986 | Munier et al. |
| 4,712,870 | A | 12/1987 | Robinson et al. |
| 4,756,605 | A | 7/1988 | Okada et al. |
| 4,772,094 | A | 9/1988 | Sheiman |
| 4,774,537 | A | 9/1988 | Moody |
| D298,250 | S | 10/1988 | Kildall |
| 4,787,733 | A | 11/1988 | Silva |
| 4,787,903 | A | 11/1988 | Grendahl |
| 4,795,248 | A | 1/1989 | Okada et al. |
| 4,813,777 | A | 3/1989 | Rainville et al. |
| 4,818,095 | A | 4/1989 | Takeuchi |
| 4,836,652 | A | 6/1989 | Oishi et al. |
| 4,842,400 | A | 6/1989 | Klein |
| 4,869,588 | A | 9/1989 | Frieder et al. |
| 4,873,029 | A | 10/1989 | Blum |
| 4,880,300 | A | 11/1989 | Payner et al. |
| 4,890,903 | A | 1/1990 | Treisman et al. |
| 4,904,063 | A | 2/1990 | Okada et al. |
| 4,906,626 | A | 3/1990 | Purvis et al. |
| 4,907,860 | A | 3/1990 | Noble |
| 4,909,626 | A | 3/1990 | Purvis et al. |
| 4,919,520 | A | 4/1990 | Okada et al. |
| 4,921,728 | A | 5/1990 | Takiguchi |
| 4,927,241 | A | 5/1990 | Kuijk |
| 4,929,865 | A | 5/1990 | Blum |
| 4,930,884 | A | 6/1990 | Tichenor et al. |
| 4,944,584 | A | 7/1990 | Maeda et al. |
| 4,945,242 | A | 7/1990 | Berger et al. |
| 4,952,048 | A | 8/1990 | Frieder et al. |
| 4,952,788 | A | 8/1990 | Berger et al. |
| 4,955,712 | A | 9/1990 | Barth et al. |
| 4,961,639 | A | 10/1990 | Lazarus |
| 4,958,907 | A | 11/1990 | Davis |
| 4,968,127 | A | 11/1990 | Russell et al. |
| 4,981,342 | A | 1/1991 | Fiala |
| 4,991,951 | A | 2/1991 | Mizuno et al. |
| 5,015,086 | A | 5/1991 | Okaue et al. |
| 5,030,882 | A | 7/1991 | Solero |
| 5,050,981 | A | 9/1991 | Roffman |
| 5,066,301 | A | 11/1991 | Wiley |
| 5,073,021 | A | 12/1991 | Marron |
| 5,076,665 | A | 12/1991 | Petersen |
| 5,089,023 | A | 2/1992 | Swanson et al. |
| 5,091,801 | A | 2/1992 | Ebstein |
| 5,108,169 | A | 4/1992 | Mandell |
| 5,114,628 | A | 5/1992 | Hofer et al. |
| 5,130,856 | A | 7/1992 | Tichenor et al. |
| 5,142,411 | A | 8/1992 | Fiala |
| 5,147,585 | A | 9/1992 | Blum |
| 5,150,234 | A | 9/1992 | Takahashi et al. |
| 5,171,266 | A | 12/1992 | Wiley et al. |
| 5,178,800 | A | 1/1993 | Blum |
| 5,182,585 | A | 1/1993 | Stoner |
| 5,184,156 | A | 2/1993 | Black et al. |
| 5,200,859 | A | 4/1993 | Payner et al. |
| 5,208,688 | A | 5/1993 | Fergason et al. |
| 5,219,497 | A | 6/1993 | Blum |
| 5,229,797 | A | 7/1993 | Futhey et al. |
| 5,229,885 | A | 7/1993 | Quaglia |
| 5,231,430 | A | 7/1993 | Kohayakawa |
| 5,239,412 | A | 8/1993 | Naka et al. |
| D342,063 | S | 12/1993 | Howitt et al. |
| 5,305,028 | A | 4/1994 | Okano |
| 5,306,926 | A | 4/1994 | Yonemoto |
| 5,324,930 | A | 6/1994 | Jech, Jr. |
| 5,352,886 | A | 10/1994 | Kane |
| 5,359,444 | A | 10/1994 | Piosenka et al. |
| 5,375,006 | A | 12/1994 | Haas |
| 5,382,986 | A | 1/1995 | Black et al. |
| 5,386,308 | A | 1/1995 | Michel et al. |
| 5,424,927 | A | 6/1995 | Schaller et al. |
| 5,440,357 | A | 8/1995 | Quaglia |
| 5,443,506 | A | 8/1995 | Garabet |
| 5,451,766 | A | 9/1995 | Van Berkel |
| 5,488,439 | A | 1/1996 | Weltmann |
| 5,512,371 | A | 4/1996 | Gupta et al. |
| 5,552,323 | A | 6/1996 | Grupp |
| 5,552,841 | A | 6/1996 | Gallorini et al. |
| 5,608,567 | A | 3/1997 | Grupp |
| 5,615,588 | A | 4/1997 | Gottschald |
| 5,617,109 | A * | 4/1997 | DeJule ............... G02F 1/134309 345/100 |
| 5,668,620 | A | 9/1997 | Kurtin et al. |
| 5,682,223 | A | 10/1997 | Menezes et al. |
| 5,683,457 | A | 11/1997 | Gupta et al. |
| RE35,691 | E | 12/1997 | Theirl et al. |
| 5,702,819 | A | 12/1997 | Gupta et al. |
| 5,712,721 | A | 1/1998 | Large |
| 5,728,155 | A | 3/1998 | Anello et al. |
| 5,739,959 | A | 4/1998 | Quaglia |
| 5,742,075 | A * | 4/1998 | Burns ..................... H01L 21/84 257/59 |
| 5,777,719 | A | 7/1998 | Williams et al. |
| 5,815,233 | A | 9/1998 | Morokawa et al. |
| 5,815,239 | A | 9/1998 | Chapman et al. |
| 5,859,685 | A | 1/1999 | Gupta et al. |
| 5,861,934 | A | 1/1999 | Blum et al. |
| 5,861,936 | A | 1/1999 | Sorensen |
| 5,877,876 | A | 3/1999 | Birdwell |
| 5,900,720 | A | 5/1999 | Kallman et al. |
| 5,949,521 | A | 9/1999 | Williams et al. |
| 5,953,098 | A | 9/1999 | Lieberman et al. |
| 5,956,183 | A | 9/1999 | Epstein et al. |
| 5,963,300 | A | 10/1999 | Horwitz |
| 5,967,795 | A | 10/1999 | Bakowsky et al. |
| 5,971,540 | A | 10/1999 | Ofner |
| 5,980,037 | A | 11/1999 | Conway |
| 5,999,328 | A | 12/1999 | Kurtin et al. |
| 6,040,947 | A | 3/2000 | Kurtin et al. |
| 6,050,687 | A | 4/2000 | Bille et al. |
| 6,069,742 | A | 5/2000 | Silver |
| 6,086,203 | A | 7/2000 | Blum et al. |
| 6,086,204 | A | 7/2000 | Magnante |
| 6,095,651 | A | 8/2000 | Williams et al. |
| 6,099,117 | A | 8/2000 | Gregory |
| 6,115,177 | A | 9/2000 | Vossler |
| 6,139,148 | A | 10/2000 | Menezes |
| 6,145,987 | A | 11/2000 | Baude et al. |
| 6,188,525 | B1 | 2/2001 | Silver |
| 6,191,881 | B1 | 2/2001 | Tajima |

(56) References Cited

U.S. PATENT DOCUMENTS

| | | |
|---|---|---|
| 6,199,984 B1 | 3/2001 | Menezes |
| 6,213,602 B1 | 4/2001 | Smarto |
| 6,270,220 B1 | 8/2001 | Keren |
| 6,271,915 B1 | 8/2001 | Frey et al. |
| 6,305,802 B1 | 10/2001 | Roffman et al. |
| 6,325,508 B1 | 12/2001 | Decreton et al. |
| 6,350,031 B1 | 2/2002 | Lashkari et al. |
| 6,390,623 B1 | 5/2002 | Kokonaski et al. |
| 6,396,622 B1 | 5/2002 | Alden |
| 6,437,762 B1 | 8/2002 | Birdwell |
| 6,437,925 B1 | 8/2002 | Nishioka |
| 6,464,363 B1 | 10/2002 | Nishioka et al. |
| 6,491,394 B1 | 12/2002 | Blum et al. |
| 6,501,443 B1 | 12/2002 | McMahon |
| 6,554,425 B1 | 4/2003 | Roffman et al. |
| 6,577,434 B2 | 6/2003 | Hamada |
| 6,609,794 B2 | 8/2003 | Levine |
| 6,614,408 B1 | 9/2003 | Mann |
| 6,616,275 B1 | 9/2003 | Dick et al. |
| 6,616,279 B1 | 9/2003 | Davis et al. |
| 6,618,208 B1 | 9/2003 | Silver |
| 6,626,532 B1 | 9/2003 | Nishioka et al. |
| 6,631,001 B2 | 10/2003 | Kuiseko |
| 6,652,096 B1 | 11/2003 | Morris et al. |
| 6,654,786 B1 | 11/2003 | Fox et al. |
| 6,682,195 B2 | 1/2004 | Dreher |
| 6,709,105 B2 | 3/2004 | Menezes |
| 6,709,107 B2 | 3/2004 | Jiang et al. |
| 6,709,108 B2 | 3/2004 | Levine et al. |
| 6,738,199 B2 | 5/2004 | Nishioka |
| 6,768,536 B2 | 7/2004 | Okuwaki et al. |
| 6,774,871 B2 | 8/2004 | Birdwell |
| 6,778,246 B2 | 8/2004 | Sun et al. |
| 6,793,340 B1 | 9/2004 | Morris et al. |
| 6,833,938 B2 | 12/2004 | Nishioka |
| 6,840,619 B2 | 1/2005 | Dreher |
| 6,851,805 B2 | 2/2005 | Blum et al. |
| 6,859,333 B1 | 2/2005 | Ren et al. |
| 6,882,482 B2 | 4/2005 | Ogasawara |
| 6,883,916 B2 | 4/2005 | Menezes |
| 6,886,938 B1 | 5/2005 | Menezes |
| 6,893,124 B1 | 5/2005 | Kurtin |
| 6,902,271 B2 | 6/2005 | Perrott et al. |
| 6,918,670 B2 | 7/2005 | Blum et al. |
| 6,948,818 B2 | 9/2005 | Williams et al. |
| 6,951,391 B2 | 10/2005 | Morris et al. |
| 6,955,433 B1 | 10/2005 | Wooley et al. |
| 6,956,682 B2 | 10/2005 | Wooley |
| 6,986,579 B2 | 1/2006 | Blum et al. |
| 7,008,054 B1 | 3/2006 | Kurtin et al. |
| 7,009,757 B2 | 3/2006 | Nishioka et al. |
| 7,019,890 B2 | 3/2006 | Meredith et al. |
| 7,041,133 B1 | 5/2006 | Azar |
| 7,085,065 B2 | 8/2006 | Silver |
| 7,133,172 B2 | 11/2006 | Nishioka |
| 7,159,981 B2 | 1/2007 | Kato |
| 7,159,983 B2 | 1/2007 | Menezes et al. |
| 7,209,097 B2 | 4/2007 | Suyama |
| 7,229,173 B2 | 6/2007 | Menezes et al. |
| 7,327,434 B1 | 2/2008 | Ren et al. |
| 7,393,472 B2 | 7/2008 | Lee et al. |
| 7,532,303 B2 | 5/2009 | Kato et al. |
| 8,154,804 B2 | 4/2012 | McGinn et al. |
| 9,280,020 B2 | 3/2016 | Bos et al. |
| 2001/0055094 A1 | 12/2001 | Zhang |
| 2002/0140899 A1 | 10/2002 | Blum et al. |
| 2002/0145701 A1* | 10/2002 | Sun .................. G02F 1/134309 349/200 |
| 2002/0149739 A1 | 10/2002 | Perrott et al. |
| 2002/0186346 A1 | 12/2002 | Stantz et al. |
| 2003/0018383 A1 | 1/2003 | Azar |
| 2003/0151721 A1 | 8/2003 | Lai et al. |
| 2003/0210377 A1 | 11/2003 | Blum et al. |
| 2004/0008319 A1 | 1/2004 | Lai et al. |
| 2004/0108971 A1 | 6/2004 | Waldern et al. |
| 2004/0117011 A1 | 6/2004 | Aharoni et al. |
| 2004/0130677 A1 | 7/2004 | Liang et al. |
| 2004/0179280 A1 | 9/2004 | Nishioka |
| 2004/0196435 A1 | 10/2004 | Dick et al. |
| 2004/0223113 A1 | 11/2004 | Blum et al. |
| 2004/0246440 A1 | 12/2004 | Andino et al. |
| 2005/0036109 A1 | 2/2005 | Blum et al. |
| 2005/0073739 A1 | 4/2005 | Meredith |
| 2005/0124983 A1 | 6/2005 | Frey et al. |
| 2006/0044510 A1 | 3/2006 | Williams et al. |
| 2006/0164593 A1 | 7/2006 | Peyghambarian |
| 2006/0273284 A1 | 12/2006 | Hirose |
| 2007/0146862 A1 | 6/2007 | Moore et al. |
| 2007/0268417 A1 | 11/2007 | Kato et al. |
| 2007/0279365 A1 | 12/2007 | Kageyama |
| 2008/0212007 A1 | 9/2008 | Meredith |
| 2008/0266473 A1 | 10/2008 | Osawa et al. |
| 2009/0207147 A1* | 8/2009 | Perrot .................. G06F 1/3215 345/173 |
| 2009/0279050 A1* | 11/2009 | McGinn ................. G02C 7/061 351/159.47 |
| 2010/0105105 A1 | 4/2010 | Azucena et al. |
| 2011/0025955 A1* | 2/2011 | Bos .................. G02F 1/134309 349/95 |
| 2011/0233475 A1* | 9/2011 | Foley .................. H01B 3/004 252/500 |
| 2013/0135578 A1* | 5/2013 | Pugh ........................ G02C 7/04 351/159.39 |
| 2014/0132904 A1* | 5/2014 | Bos .................. G02F 1/134309 349/139 |
| 2015/0036096 A1 | 2/2015 | Kadomi et al. |
| 2016/0000557 A1* | 1/2016 | Galstian .................... A61F 2/16 623/6.22 |
| 2017/0276740 A1* | 9/2017 | Schmitt .................... G01D 5/16 |

FOREIGN PATENT DOCUMENTS

| | | | |
|---|---|---|---|
| DE | 4222395 A1 | 1/1994 | |
| EP | 0154962 A3 | 9/1985 | |
| EP | 0233104 A1 | 8/1987 | |
| EP | 0237365 A1 | 9/1987 | |
| EP | 0258996 A2 | 3/1988 | |
| EP | 0578833 A1 | 1/1994 | |
| EP | 1511023 A2 | 3/2005 | |
| GB | 2169417 A | 7/1986 | |
| GB | 2170613 A | 8/1986 | |
| JP | 55-076323 | 6/1980 | |
| JP | 61156227 | 7/1986 | |
| JP | 01237610 A2 | 9/1989 | |
| JP | 7028002 | 1/1995 | |
| JP | 11352445 A | 12/1999 | |
| JP | 2004334031 | 11/2004 | |
| JP | 2005071424 | 3/2005 | |
| JP | 2006092968 | 4/2006 | |
| JP | 2007322710 | 12/2007 | |
| JP | 2007323062 | 12/2007 | |
| JP | 2008076926 | 4/2008 | |
| JP | 2009157145 A | 7/2009 | |
| JP | 2011180373 A | 9/2011 | |
| WO | WO 92/01417 A1 | 2/1992 | |
| WO | WO 93/21010 A1 | 10/1993 | |
| WO | WO 98/27863 A1 | 7/1998 | |
| WO | WO 99/27334 A1 | 6/1999 | |
| WO | WO 03/050472 A1 | 6/2003 | |
| WO | WO 03/068059 A2 | 8/2003 | |
| WO | WO 2004/008189 A1 | 1/2004 | |
| WO | WO 2004/015481 A1 | 2/2004 | |
| WO | WO 2004/034095 A3 | 4/2004 | |
| WO | WO 2004/072687 A2 | 8/2004 | |
| WO | WO 2006/092968 A1 | 9/2006 | |
| WO | WO 2008/027890 A2 | 3/2008 | |

OTHER PUBLICATIONS

Anderson, M., "Adaptive Optics: Liquid Crystals Lower the Cost of Adaptive Optics," Laser Focus World, Dec. 1999, 7 pages.

(56) References Cited

OTHER PUBLICATIONS

Bird, J. O., Electrical Circuit Theory and Technology, Oxford: Newnes, Aug. 2007, p. 510-514.
Bradley, A., "Profile: Larry N. Thibos, Ph.D. and Donald T. Miller, Ph.D.," *Indiana Journal of Optometry* 1999, vol. 2, No. 1, p. 5.
Davis, R. A., "Computer Vision Syndrome—The Eyestrain Epidemic," *Review of Optometry*, Sep. 15, 1997, 7 pages.
Eyecare Business, Oct. 1997, 76 pages.
Haddock, J. N., "Liquid Crystal Based-Electro-Optic Diffractive Spectacle Lenses and Low Operating voltage Nematic Liquid Crystals," The University of Arizona 2005, pp. 1-131.
Hatcher, M., "Liquid Lenses Eye Commercial Breakthrough," *Opto & Laser Europe*, Nov. 2003, pp. 17-18.
Hope, G. M. et al., "Night myopia," *Surv. Ophthalmology*, Sep.-Oct. 1984, vol. 29, No. 2, pp. 129-136.
Jackson, J. D., Classical Electrodynamics, New York 1999, Wiley, pp. 117-119, 125-127, 129-134, 139, 141.
Kotova, S. P. et al., "Modal Liquid Crystal Wavefront Corrector," *Optics Express*, Nov. 4, 2002, vol. 10, No. 22, pp. 1258-1272.
Kowel, S. T. et al., "Focusing by electrical modulation of refraction in a liquid crystal cell," *Applied Optics*, Jan. 15, 1984, vol. 23, No. 2, pp. 278-289.
Lazarus, S. M., "The Use of Yoked Base-Up and Base-In Prism for Reducing Eye Strain at the Computer," *Journal of the American Optometric Association*, Apr. 1996, pp. 204-208.
Loktev, M. U. et al., "Wave front control systems based on modal liquid crystal lenses," *Review of Scientific Instruments*, Sep. 2000, vol. 71, No. 9, pp. 3290-3297.
Miller, D. T. et al., "Requirements for Segmented Spatial Light Modulators for Diffraction Limited Imaging Through Aberrated Eyes," Adaptive Optics Conference, Jul. 12-16, 1999, pp. 63-68.
Naumov, A. F., "Liquid Crystal Adaptive Lenses with Modal Control," *Optics Letters*, Jul. 1, 1998, vol. 23, No. 13, pp. 992-994.
Naumov, A. F. et al., "Control optimization of spherical modal liquid crystal lenses," *Optics Express*, Apr. 26, 1999, vol. 4, No. 9, pp. 344-352.
Owens, D. A. et al., "Night myopia: cause and a possible basis or amelioration," *Am. J. Optometric Physio. Opt.* 1976, vol. 53, No. 11, pp. 709-717.
Radhakrishna, M. C. et al., "Some Properties of Indium-Tin Oxide Films," *Pramana* 1977, vol. 9, No. 1, pp. 1-6.
Richards, O. W., "Night Myopia at Night Automobile Luminances: Final Report," *Am. J. Optometric Physiology Opt.* 1978, vol. 55, No. 7, pp. 469-470.
Thibos, L. N. et al., "Vision through a liquid-crystal spatial light modulator," Adaptive Optics Conference Jul. 12-Jul. 16, 1999, Durham, UK, pp. 57-62.
Thibos, L. N. et al., "Use of a Liquid-Crystal Adaptive-Optics to Alter the Refractive State of the Eye," *Optometry and Vision Science*, Jul. 1997, vol. 74, No. 7, pp. 581-587.
Thibos, L. N. et al., "Electronic Spectacles for the 21st Century," *Indiana Journal of Optometry* 1999, vol. 2. No. 1, pp. 6-10.
Ulaby, F. T., Fundamentals of Applied Electromagnetics, Upper Saddle River, NJ, Prentice Hall 2001, pp. 157-159, 171, 282, 413.
Extended European Search Report in European Patent Application No. 16898859.0 dated Sep. 18, 2019, 7 pages.

\* cited by examiner

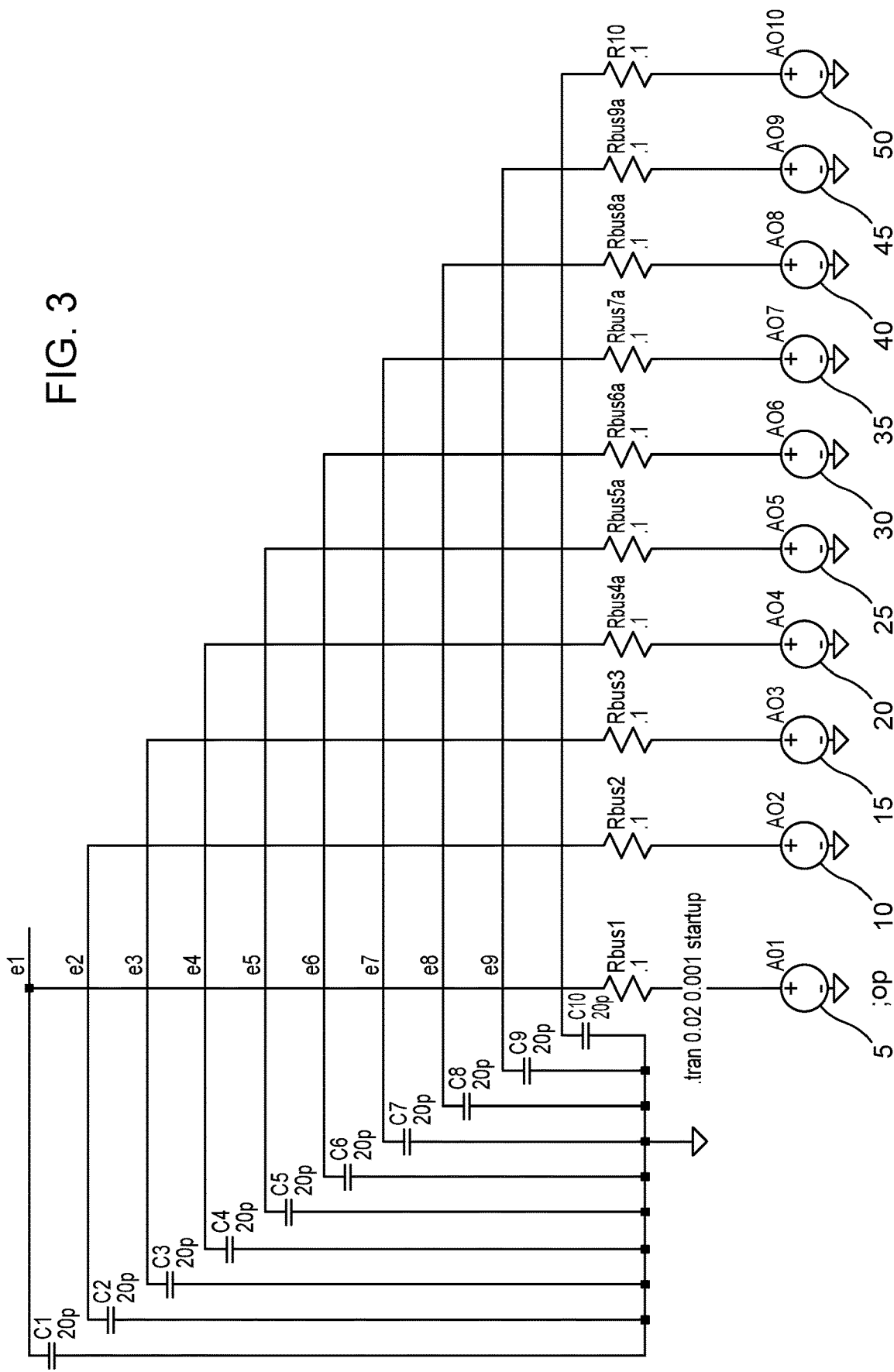

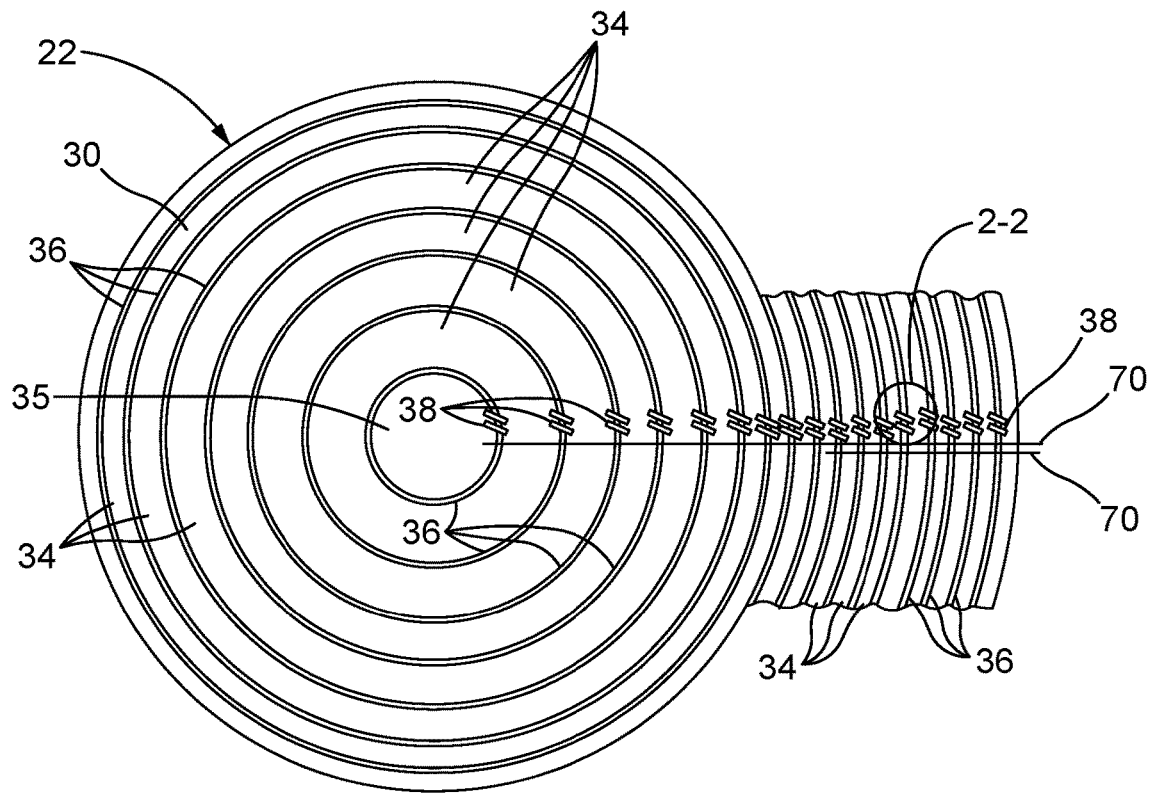
PRIOR ART
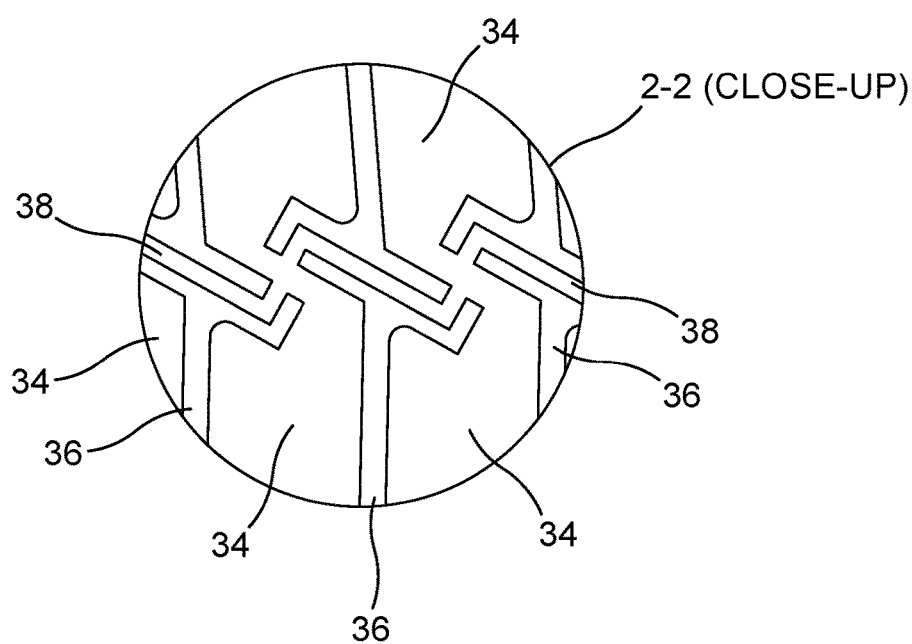
FIG. 5A

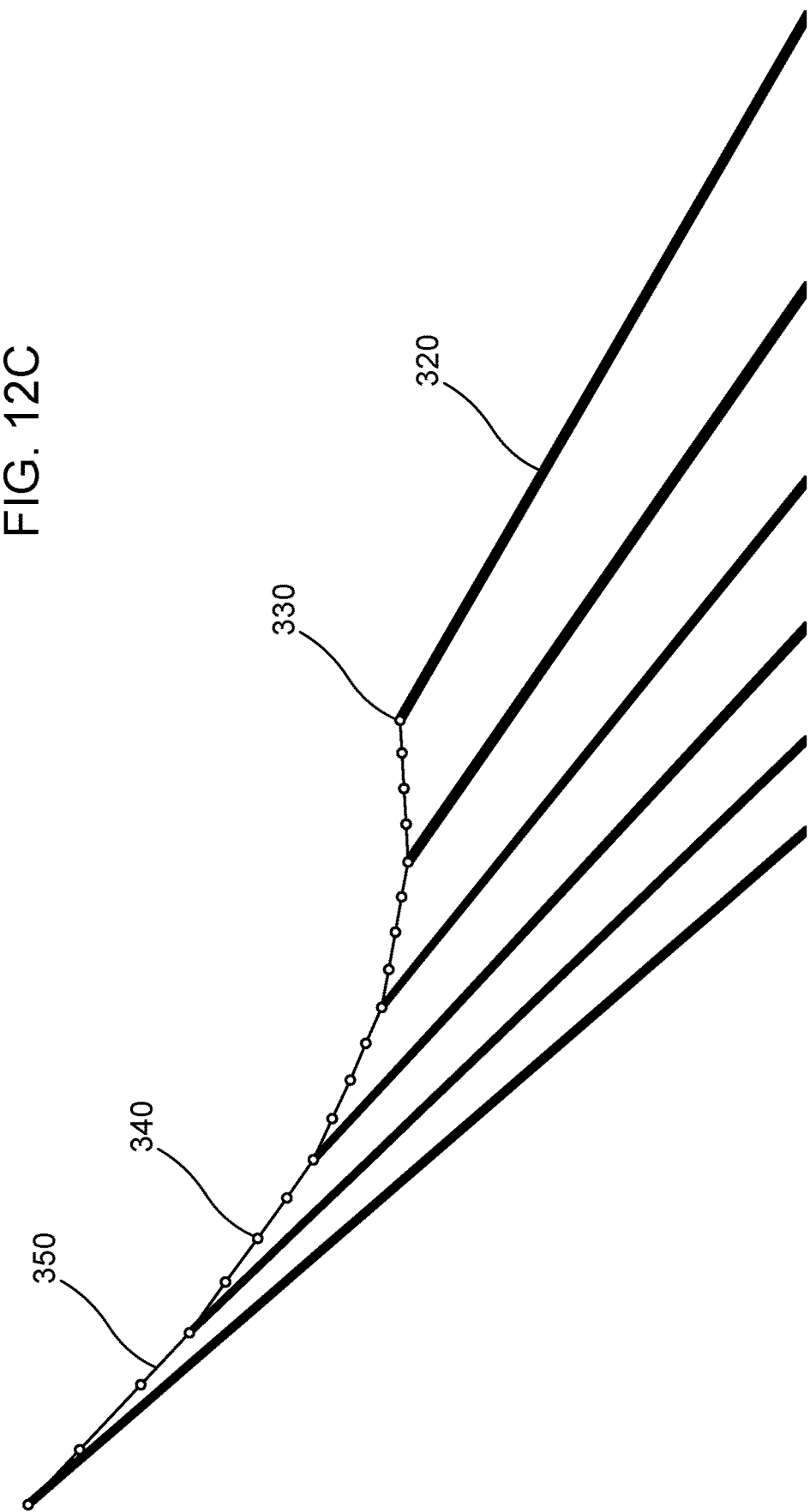

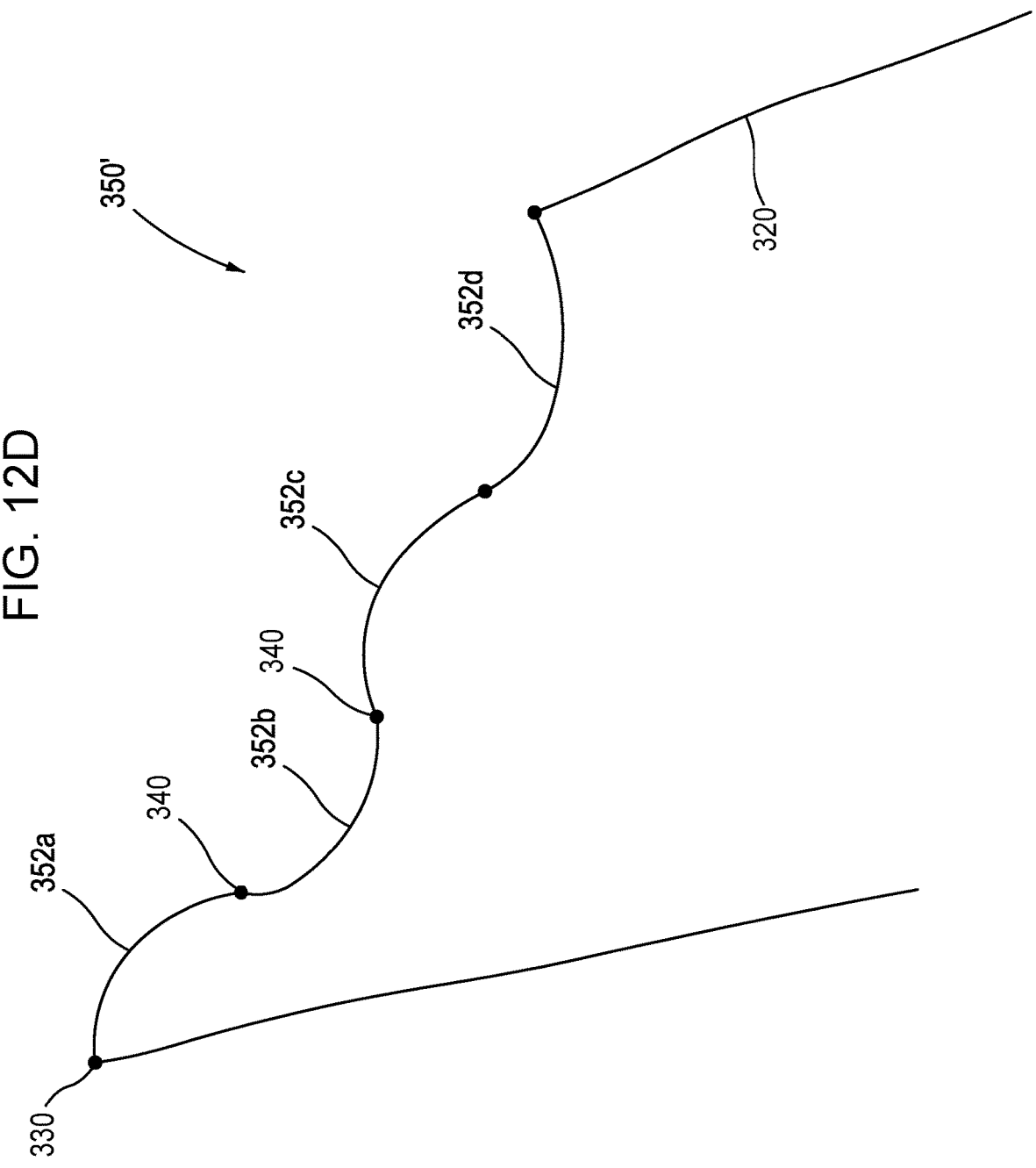

ELECTRO-ACTIVE LENSES WITH RAISED RESISTIVE BRIDGES

CROSS-REFERENCE TO RELATED APPLICATIONS

This application is a bypass continuation application of International Application No. PCT/US2016/060784, filed on Nov. 7, 2016, and entitled "ELECTRO-ACTIVE LENSES WITH RAISED RESISTIVE BRIDGES," which in turn claims the priority benefit of U.S. Application No. 62/321,501, which was filed on Apr. 12, 2016. Each of these applications is incorporated herein by reference in its entirety.

BACKGROUND

Electro-active lenses can be made by several methods, including patterning a series of concentric electrodes of conductive material on a first substrate, then sandwiching a layer of liquid crystal between the first substrate and second substrate opposite the first substrate. The second substrate may have one or more circular patterns of conductive material patterned on it, or any other shape to match or exceed the area of the patterned electrodes, allowing an electrical circuit to be formed that creates a voltage field between the two substrates. When an electrical field is applied across the electrodes, the liquid crystal material between the two substrates changes its index of refraction.

By applying a gradient of voltage fields at different electrode locations on the lens, a gradient of index of refraction may be created, creating a lens. The higher the number of electrodes that are used, the finer the resolution of gradient of refractive index can be created. This results in a smoother wavefront curvature, and hence provides a better quality optic.

However, increasing the number the electrodes also increases the complexity of the electronics as well as the light-blocking elements that supply power to the electrodes, so methods have been developed to allow a small number of power supply lines to apply a voltage gradient across a larger number of electrodes. In particular, N power supply lines can be used to apply a voltage gradient across M>N electrodes with resistive bridges between the electrodes. In these electro-active lenses, every M/Nth electrode is connected to a power supply line, and the other electrodes are coupled to each other with resistive bridges.

In conventional electro-active lenses with resistive bridges, the resistive bridges are made in such a manner that the electrode ring is no longer continuous, degrading optical quality. The problem can be partially solved by fabricating the resistive bridges in the same plane as the electrodes, locating the resistors in between adjacent electrodes. In some cases, there are additional shortcomings, including the use of extremely high resistive materials, which are difficult to manufacture in a controllable manner, and the need to fill the entire gap between electrodes with resistive material is required to fill a large area. In general, it is desirable to reduce the gap between electrodes to improve optical performance, but this can exacerbate the difficulty of manufacturing the resistive components.

SUMMARY

The inventors have recognized that prior-art solutions to the problem of reducing the complexity of the drive channels in electro-active lenses have introduced a new problem: excessive power consumption of the electro-active lenses. Without resistive bridges, a typical lens design may consume only nano-amperes of electrical current. However, the resistive bridges provide a pathway for the electrical current to flow from one drive channel to the others. This extra current flow leads to an undesired increase in the power consumption of the electro-active lens.

The inventors have recognized that increasing the resistance of the resistive bridges reduces this increased power consumption. In some cases, the resistance can be increased by increasing the resistor's size. But fitting the larger resistor into the same plane as the electrodes means that the gaps between the electrodes must be larger, the electrodes must be interrupted, or both for the larger resistor to fit.

Unfortunately, creating a larger, high resistance bridge in such a small space very difficult. In addition, interruptions in the electrodes gaps degrade the lens's optical performance: etching away a portion of the electrode to make space for the resistive bridge degrades the integrity of the electrodes and hence the optical performance of the lens. To further compound the problem, the gap between electrodes is a dimension that should be reduced as much as possible in order to reduce effects that degrade optical performance, further increasing the challenge of increasing the resistance of the resistance bridges.

Fortunately, the present technology addresses these problems by providing larger, higher resistance bridges that do not degrade the lens's optical performance. In these designs, the electrodes can remain continuous and close together. In addition, there is no need to remove or sacrifice surface area from the electrodes to make room for the resistive bridges. Embodiments of the present technology include an electro-optic lens comprising a first substantially transparent substrate, a plurality of electrodes disposed on a surface of the first substantially transparent substrate, an insulating layer disposed on the plurality of electrodes, and a resistive bridge disposed on the insulating layer. The resistive bridge connects a first electrode in the plurality of electrodes with a second electrode in the plurality of electrodes via holes patterned into the insulating layer. In operation, applying a voltage to the first electrode via the resistive bridge causes an electro-active material, such as (bi-stable) liquid crystal, to change its refractive index.

The plurality of electrodes may comprise a plurality of concentric ring electrodes, with the first electrode being a first concentric ring electrode and the second electrode being a second concentric ring electrode. In these cases, the first concentric ring electrode can have a constant width.

The plurality of electrodes may be formed a first material having a first sheet resistance and the resistive bridge may be formed of a second material having a second sheet resistance higher than the first sheet resistance.

There may be insulating material disposed between the first electrode and the second electrode. This insulating layer may span a gap between the first electrode and the second electrode of less than about 3 microns.

The resistive bridge can have a resistance of at least about 2.5 MΩ and a length-to-width ratio of about 25:1. The resistive bridge may include nickel, chromium, indium tin oxide, resistive polymer (e.g., PEDOT:PSS), or any combination or alloy thereof.

The resistive bridge can comprise a plurality of resistive segments, with each resistive segment in the plurality of resistive segments being in electrical communication with a corresponding pair of electrodes in the plurality of electrodes. The plurality of resistive segments can include a first resistive segment with a first width and a second resistive segment with a second width greater than the first width. The plurality of resistive segments can also include a first resistive segment with a first length and a second resistive segment with a second length greater than the first length. And at least one resistive segment in the plurality of resistive segments may have a curved or bent edge.

Embodiments of the present technology also include a method of making an electro-optic lens. In one example of this method, a plurality of electrodes is formed on a substrate. A layer of insulating material is deposited on the electrodes. Next, a plurality of through holes is formed in the layer of insulating material. Each through hole in the plurality of through holes connects to a corresponding electrode in the plurality of electrodes. A resistive material is deposited on the layer of insulating material and in the plurality of through holes. And the resistive material is patterned to form a plurality of resistors. Each resistor in the plurality of resistors connects to a corresponding electrode in the plurality of electrodes. Optionally, a buss line can be formed in electrical communication with the electrodes and resistors.

In some cases, forming the plurality of electrodes comprises forming a plurality of concentric ring electrodes. In these cases, forming the plurality of concentric ring electrodes may comprise forming a first concentric ring electrode separated from a second concentric ring electrode by a gap of less than about 3 microns. Each concentric ring electrode may have a constant width (with the widths being the same or different among the concentric ring electrodes).

The resistive material may have a sheet resistance higher than a sheet resistance of the plurality of electrodes. It may be patterned to form at least one resistor having a resistance of at least about 2.5 MΩ, at least one resistor having a length-to-width ratio of about 25:1, or both. In some cases, there may be a first resistor with a first width and a second resistor segment with a second width greater than the first width. Likewise, there may be a first resistor with a first length and a second resistor with a second length greater than the first length. The resistive material may be patterned to form at least one resistor with a curved edge.

Another embodiment includes an electro-active contact lens with a base optical element and an electro-active element embedded within the base optical element. The electro-active element includes a plurality of electrodes, an insulating layer disposed on the plurality of electrodes, and a resistive bridge disposed on the insulating layer. The resistive bridge connects a first electrode in the plurality of electrodes with a second electrode in the plurality of electrodes via holes patterned into the insulating layer.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 3 shows an electrical schematic of an electro-active lens without resistive bridges.

FIG. 5A shows a plan view of an electro-active lens with in-plane resistive bridges.

FIGS. 12A-12C show different views of the electrodes, resistors, and buss lines of the electro-active lens of FIG. 11.

FIG. 12D shows a raised resistive bridge with curved bridge segments.

DETAILED DESCRIPTION

This application discloses electro-active lenses, including electro-active contact lenses and electro-active intraocular lenses, with electrodes connected with raised resistive bridges. For instance, the resistive bridges can be disposed on an insulating layer about the electrodes. Placing the resistive bridges and electrodes on opposite sides of an insulating layer offers many advantages over electro-active lenses without resistive bridges and electro-active lenses with conventional resistive bridges. Compared to an electro-active lens without resistive bridges, an electro-active lens with raised resistive bridges can support more electrodes with fewer buss lines. And compared to an electro-active lens with conventional resistive bridges, an electro-active lens with raised resistive bridges can support ring electrodes that are both continuous and closer together because the resistors aren't disposed between the ring electrodes. Continuous, closely spaced electrodes offer better optical performance than discontinuous or widely spaced electrodes.

A raised resistive bridge can be larger too, which means that it is less likely to break when flexed due its larger surface area. A larger raised resistive bridge also has higher resistance and lower power consumption as explained below. In a contact lens or intraocular lens, low power consumption is especially beneficial because of limited available power in such a small device and its subsequently small size battery of power storage device. These raised resistive bridges enable lower power consumption while preserving the optical capabilities that the device's design provides.

In addition, an electro-active lens with raised resistive bridges can be fabricated more easily than an electro-active lens with conventional resistive bridges because raised resistive bridges don't have to be as precisely sized, shaped, or positioned as conventional resistive bridges. Put differently, a raised resistive bridge can be made with coarser resolution features because it goes over the electrodes and is not part of the optical area. As a result, an electro-active lens with raised resistive bridges can be made using simpler lithography or inkjet printing on flexible surfaces. And because it is on a different level than the electrodes, a raised resistive bridge can also be made from different materials than the electrodes. For instance, the electrodes may be made from a conductive, transparent material, such as indium tin oxide (ITO), and the raised resistive bridge may be made of a material with a higher resistivity than ITO.

Electro-Active Lenses without Resistive Bridges

Figure 1:
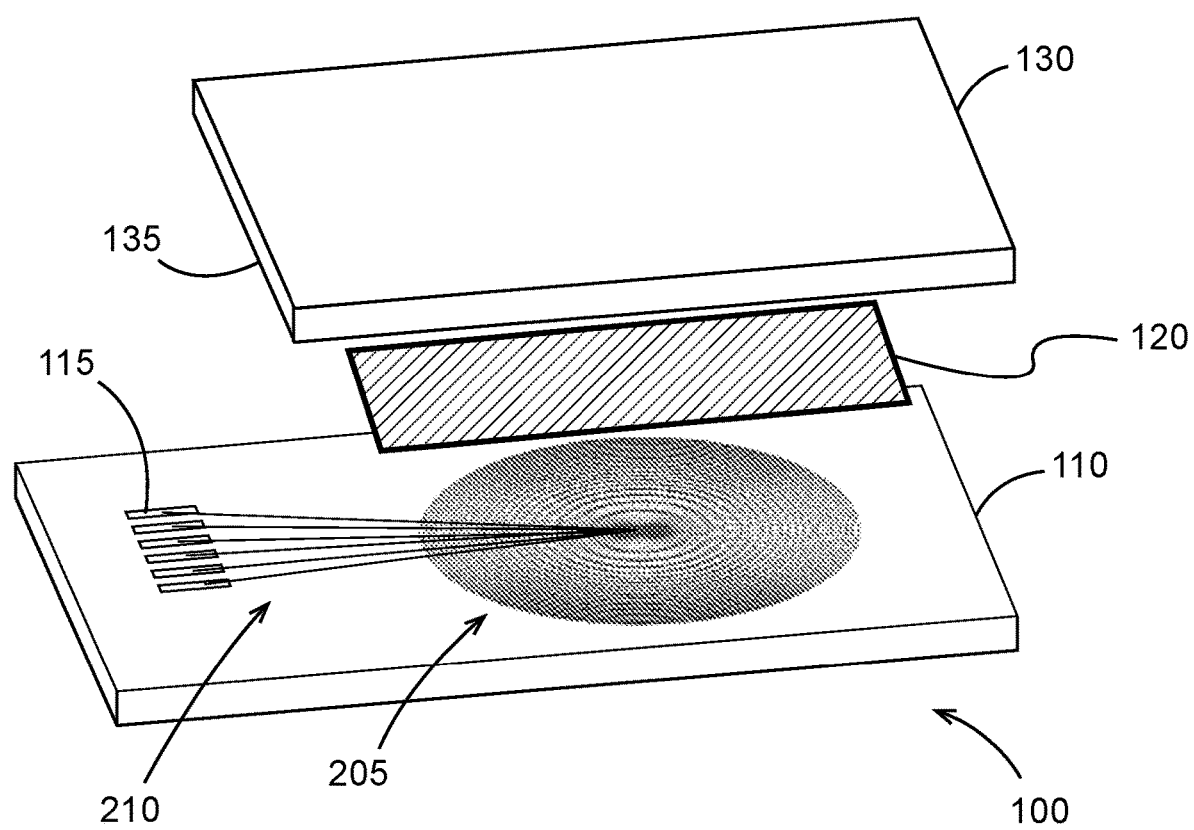
FIG. 1 shows an electro-active lens without resistive bridges between electrodes.

FIG. 1 shows an exploded, perspective view of an electro-active lens 100 without resistive bridges. The electro-active lens 100 includes a lower substrate 110 patterned with a set of concentric ring electrodes 205 and conductive connection pads 115. Conductive buss lines 210 connect respective electrodes 205 with respective conductive connection pads 115. The electrodes 205, buss lines 220, and connection pads 115 may be formed of a transparent conductive material, such as indium tin oxide (ITO), that is deposited onto the lower substrate 110 and patterned using standard lithographic techniques. An upper substrate 130 forms the other half of the lens 110. The underside of the upper substrate 130 is coated with a layer of transparent conductive material that acts as another electrode (e.g., a ground plane 135). A layer of liquid crystal material 120 is sandwiched between the upper substrate 130 and the lower substrate 120 to form the lens 110.

In operation, the individually controllable voltage at each buss line 220 may be utilized to modulate the refractive index of the liquid crystal material 120 between the corresponding ring electrode 220 and the ground plane 135. For instances, the voltages applied to the buss lines 220 may be selected to generate spherical wave front when the lens 100 is positioned in the path of a plane wave. The voltages may also be selected to deviate from a sphere-only wave front. Such a deviation may be useful in correcting higher order aberrations, one example being spherical aberration.

Figure 2A:
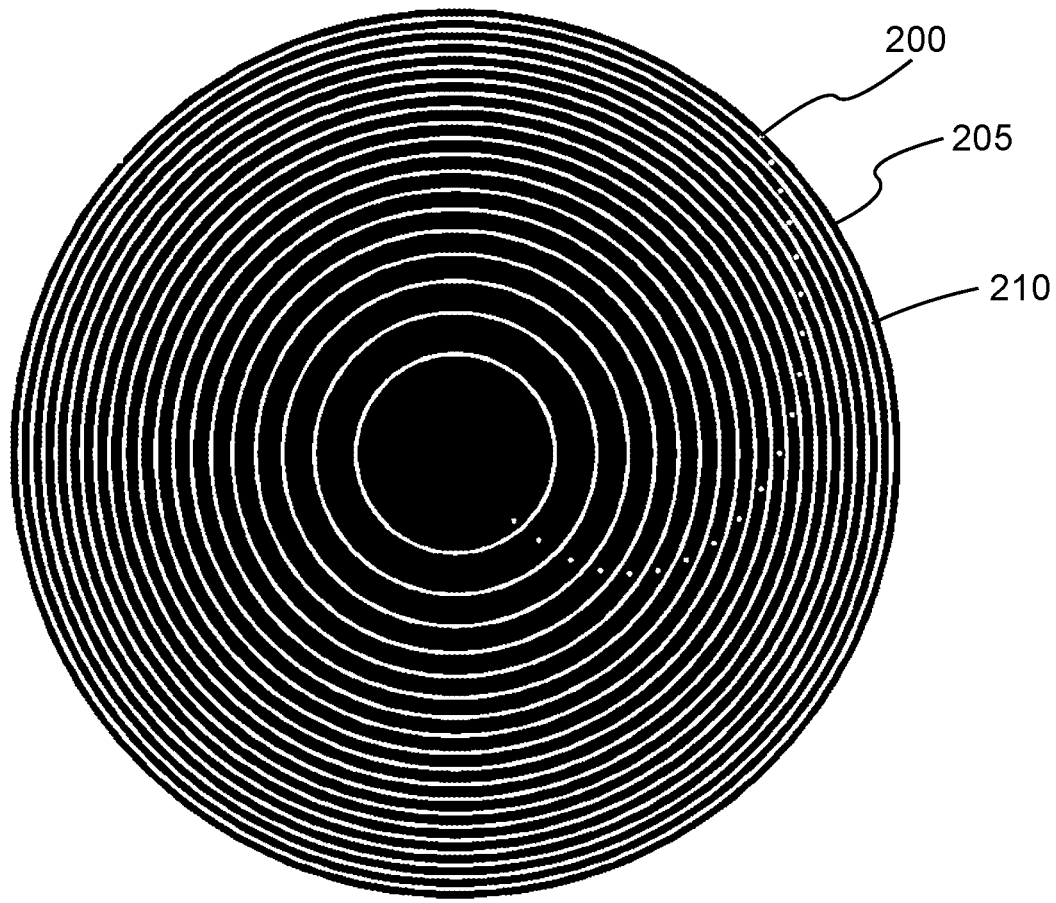
FIG. 2A shows the electrodes in the electro-active lens of FIG. 1 without the electrical connections that supply power to the electrodes.
Figure 2B:
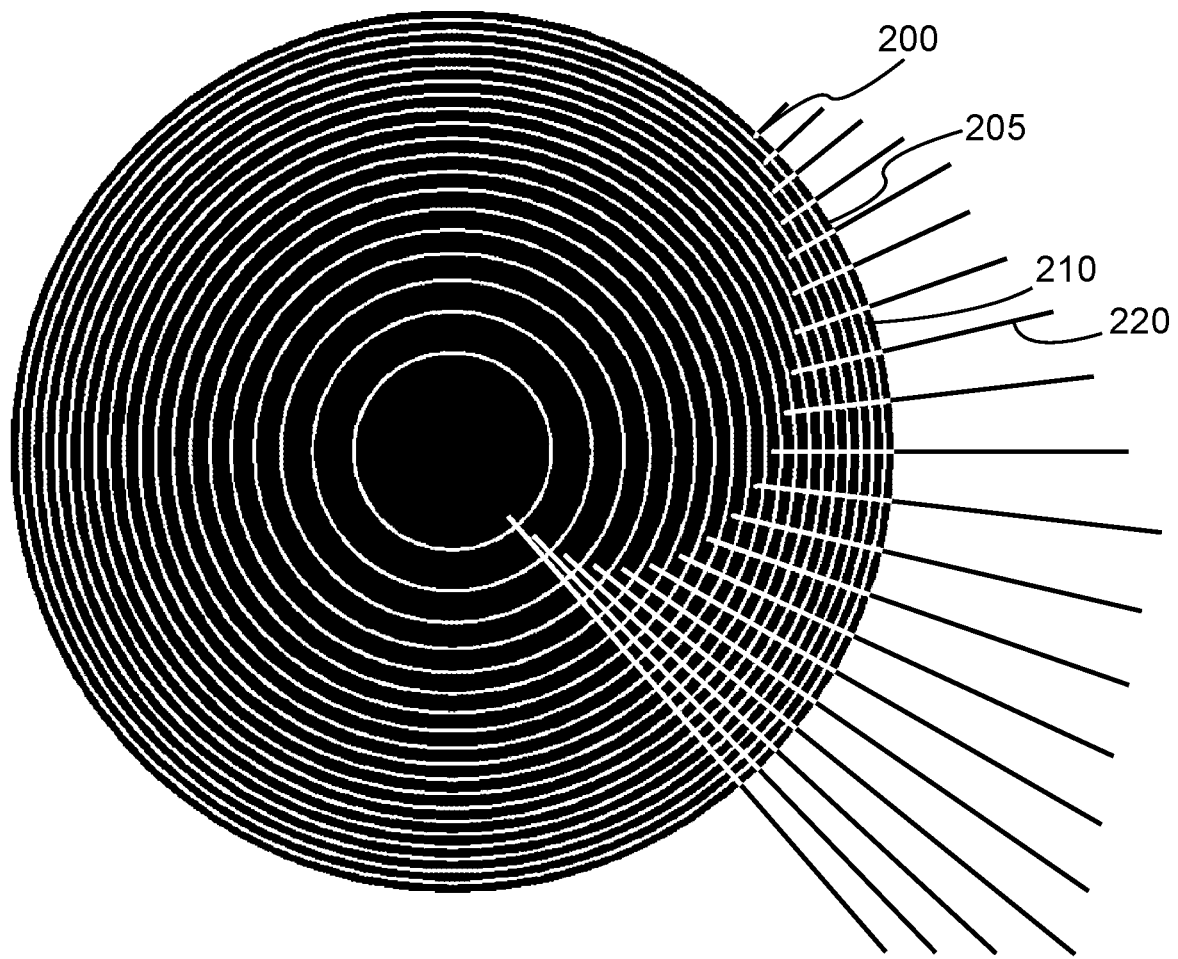
FIG. 2B shows the electrodes of FIGS. 1 and 2A with buss lines added.

FIGS. 2A and 2B show the concentric circular electrodes 205 of the electro-active lens 100 of FIG. 1 in greater detail. FIG. 2A shows the lens 100 without the electrical connections yet made to supply power to the electrodes 205. The circular electrodes 205 are typically made from a transparent but electrically conductive material such as indium tin oxide (ITO), patterned on a transparent substrate, such as glass or plastic. Between each electrode 205 is a gap 210 without conductive material to prevent electrical connection between the electrodes 205. The gaps 210 (nineteen shown) may be either left unfilled or filled with a non-conductive material, for example, silicon dioxide ($SiO_2$). In many cases, it is desirable to make this gap as small as possible, with typical gap sizes of 1 to 3 microns. Smaller or larger gaps are also possible. In this example, twenty electrodes 205 are shown, but many more are typically used, perhaps hundreds or thousands.

The lens 100 may include an insulating layer (not shown) on top of the circular electrodes 205 and gaps 210. This insulating layer may be made from a material that does not conduct electricity but is optically transparent, for example, a 125 nm thick layer of $SiO_2$ deposited over the electrodes 205. A series of holes 200 (twenty shown) are patterned in the insulating layer to expose a section of each underlying electrode 205. The purpose of these holes 200 is explained below with respect to FIG. 2B.

FIG. 2B shows the electrodes 205 with buss lines 220 (twenty shown) connected to respective electrodes 205 via respective holes 200. Buss lines 220 are made from an electrically conductive material, for example, nickel. They are typically about 10 microns wide, but can be narrower (e.g., 1 micron) if space is limited and power conduction is low or wider (e.g., 100 microns) if power conduction is higher. Each buss line 220 may be up to 10 mm long, depending on the circuit design.

In operation, the buss lines 220 provide electrical power to the electrodes 205. Each buss line 220 delivers power only to its designated electrode 205 and not to any other electrode 205. The insulating layer prevents the buss lines 220 from shorting out or connecting to the other electrodes below it, and only allows connection of the buss line 220 to the desired electrode 205 through the via hole 200 in the insulating layer.

The example lens 100 shown in FIGS. 1 and 2 uses one buss line per electrode. In this example design of twenty electrodes, providing twenty buss lines and twenty electrical drive channels is manageable, but when the lens has many more electrodes, using one buss lines per electrode can become problematic. Additional buss lines can degrade the lens's optical quality by blocking light and adding undesired diffraction sources, and every additional electrical channel adds complexity and cost to the electronics. These problems can be mitigated by adding resistors between electrodes, allowing only a subset of the electrodes to be connected to the buss lines. The electrodes that aren't connected to the buss lines are powered by current delivered via resistive bridges and adjacent electrodes. This reduces the number of buss lines and electrical drive channels, but can increase the electrical power consumption as described in greater detail below.

FIG. 3 shows a typical electrical schematic of an electro-active lens without resistive bridges (e.g., lens 100 in FIGS. 1 and 2). Drive signals are provided by analog output voltage sources 5, 10, 15, 20, 25, 30, 35, 40, 45 and 50. These voltage sources are supplied by a controller (not shown), such as an application-specific integrated circuit (ASIC) embedded or electrically coupled to the electro-active lens. Capacitors C1 through C10 on the left side of the schematic in FIG. 3 represent the capacitance created by the liquid crystal layer (not shown) modulated by the electrodes. The ground symbol shows the ground plane to be the substrate opposite to the patterned-with-electrodes substrate as well as the opposite potential of the analog outputs.

The drive signal in this example is a square wave oscillating at 100 Hz, with the peak to peak voltage amplitude being, from voltage source 5 through 50, 0.57, 0.62, 0.69, 0.76, 0.83, 0.0.92, 1.03, 1.13, 1.27 and 1.5 volts, respectively. These voltages are determined by the desired gradient of retardation in the liquid crystal to create the desired optical effect. There is a relationship between the liquid crystal response and voltage referred to as the Threshold Voltage, typically referred to as the V10-V90 specification, indicating the voltage range needed to move the liquid crystal molecules through 80% of its range. The voltages may be adjusted to compensate for other design variables, such as the distance from the electrodes to the liquid crystal or the liquid crystal layer thickness.

Figure 4:
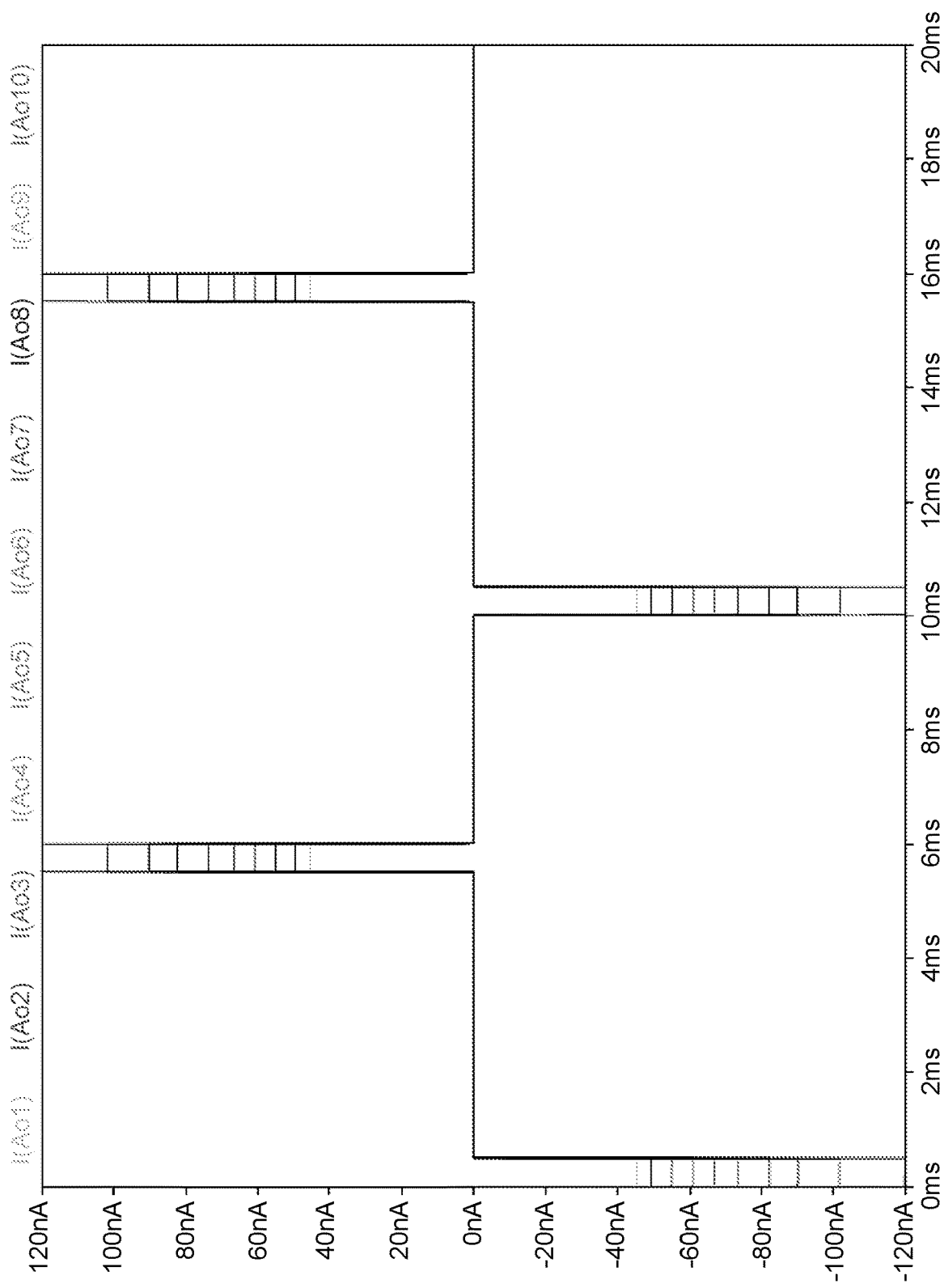
FIG. 4 shows an electrical current flow through each of the drive channels for the electro-active lens shown in FIG. 3.

FIG. 4 shows a typical electrical current flow through each of the drive channels for an electro-active lens without resistive bridges like those illustrated in FIGS. 1-3. The maximum electrical current seen is 120 nano-Amperes ($120 \times 10^{-9}$ A). If the electro-active lens's control circuitry draws another 130 nano-Amperes, this current is low enough that the lens 100 can operate for about 40 hours using a 10-microamp hour battery, which is small enough to be embedded in an electro-active ophthalmic lens, such as an electro-active contact lens or electro-active intraocular lens.

Electro-Active Lenses with In-Plane Resistive Bridges

FIG. 5A shows a plan view of electrodes 34 connected by in-plane resistive bridges 38 in a (prior art) electro-active lens from U.S. Pat. No. 9,280,020 to Bos et al., which is incorporated herein by reference in its entirety. The electrodes 34, in-plane resistive bridges 38, and a central disk electrode 35 are formed by patterning an electrode layer 30 on a substrate 22. As shown in a close-up region 2-2, the in-plane resistive bridges 38 span gaps 36 (e.g., open spaces) between adjacent electrodes 34, making it possible to reduce the number of input connections 70 between the electrodes 34 and the voltage source (not shown).

The close-up 2-2 also shows that the in-plane resistive bridges 38 create discontinuities, such as variations in width and (sharp) corners, that prevent the electrodes 34 from being perfect rings. If the resistive bridges 38 are large enough, these breaks or discontinuities can degrade the electro-active lens's optical performance and the electrode's electrical performance. Typically, in-plane resistive bridges that deliver good optical performance are typically 2 microns wide and 4 microns long. However, a resistor of this size is only about two squares of resistive material, making it difficult to use materials with a high enough resistivity or sheet resistance to provide the desired resistance to keep power consumption low as explained below. Increasing the area increases the resistance, but also necessitates a larger gap between electrodes 34, a larger discontinuity in each resistor 38, or both. As shown in FIG. 5A, intruding into the electrode 34 to lengthen the resistor 38 can provide the area to increase the resistor's length-to-width ratio so a larger amount of resistive material can be used, resulting in higher resistance, but the integrity and performance of the electrodes 34 is then compromised. The electrodes 38 shown in FIG. 5A are typically 30 microns long and 3 microns wide (about 10 squares), which provides decent resistance but degrades optical performance.

Figure 5B:
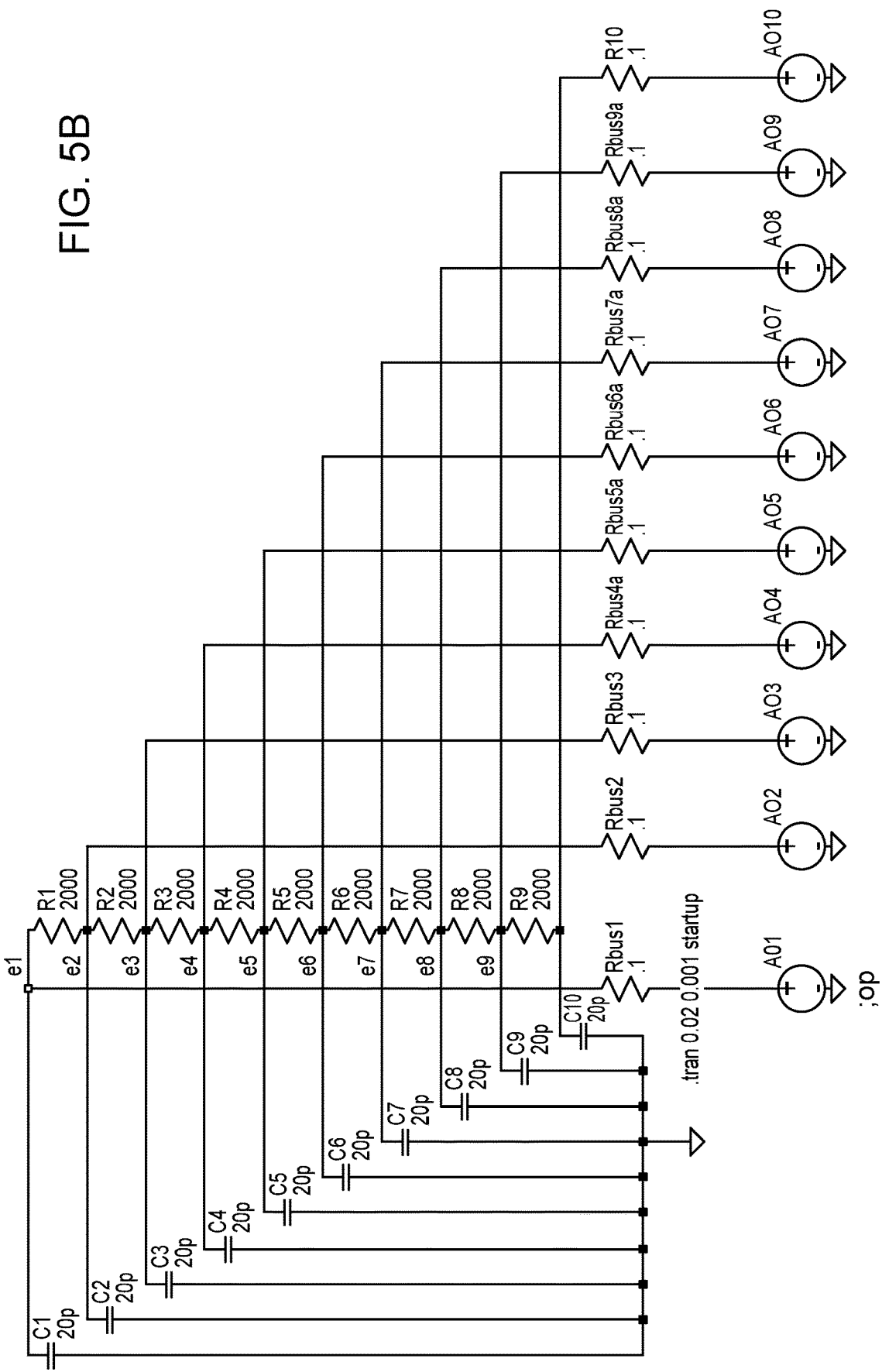
FIG. 5B shows a schematic of an electro-active lens with resistive bridges R1 through R9.

FIG. 5B shows an electrical schematic of an electro-active lens with in-plane resistive bridges R1 through R9. Each of these resistors has a resistance value of 2,000 ohms. These resistive bridges are formed in the same plane as the electrodes between adjacent electrodes. At this resistance value, they can have dimensions small enough not to degrade the electro-active lens's optical quality. That is, they are small enough to fit within the gap between electrodes and do not diffract or scatter enough incident light to obstruct or occlude a user's ability to see clearly through the lens. But the resistors increase the lens's current consumption dramatically.

Figure 6:
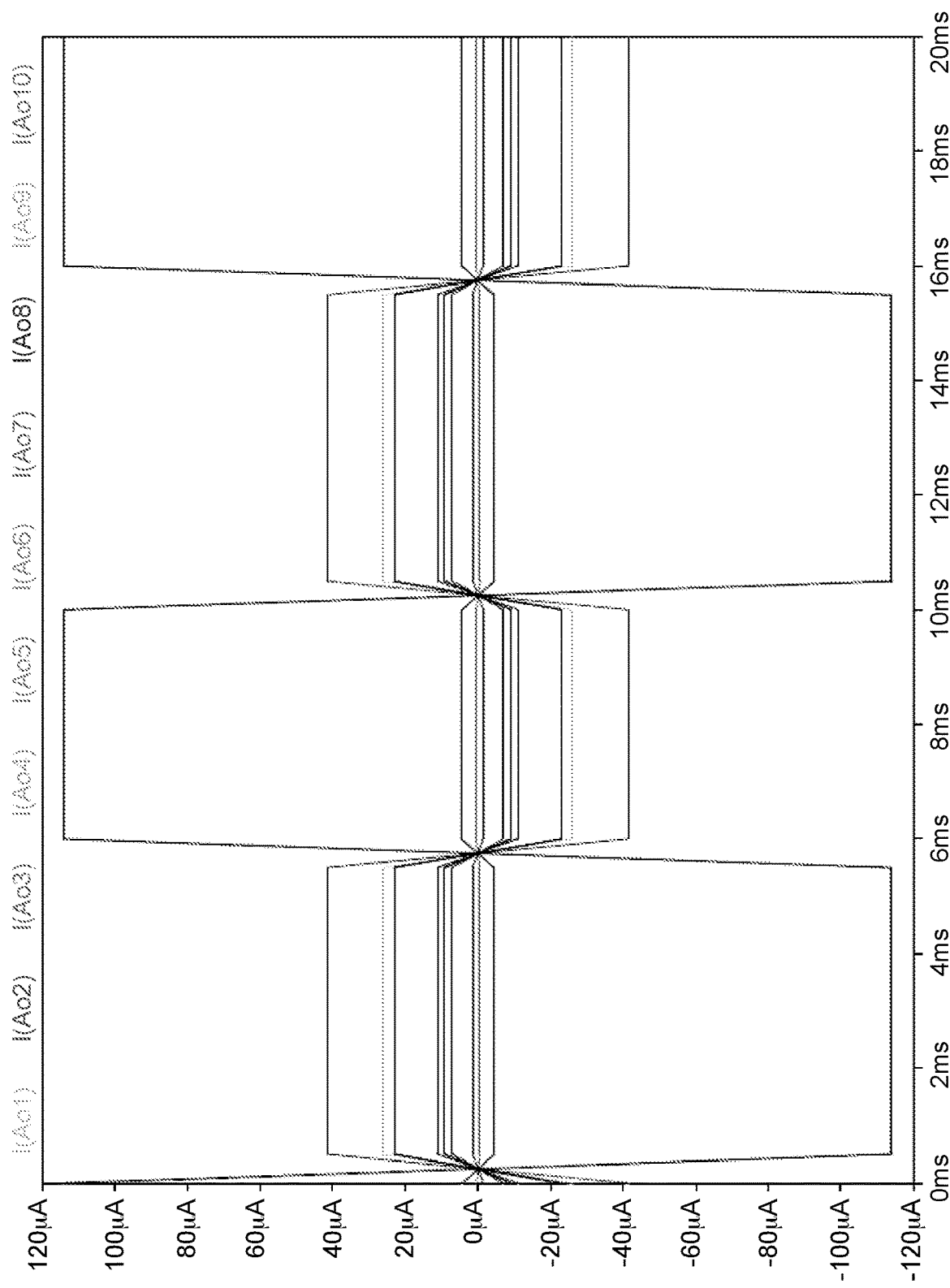
FIG. 6 shows a typical electrical current flow through each of the drive channels for the electro-active lens shown in FIG. 5.

FIG. 6 shows the typical electrical current flow through each of the drive channels for the electro-active lens shown in FIG. 5. The maximum electrical current is 117 micro-Amperes ($117 \times 10^{-6}$ A). At this current consumption, the electro-active lens would deplete a 10-microamp hour battery in about five minutes, which is too short to be practical for most ophthalmic applications.

Figure 7:
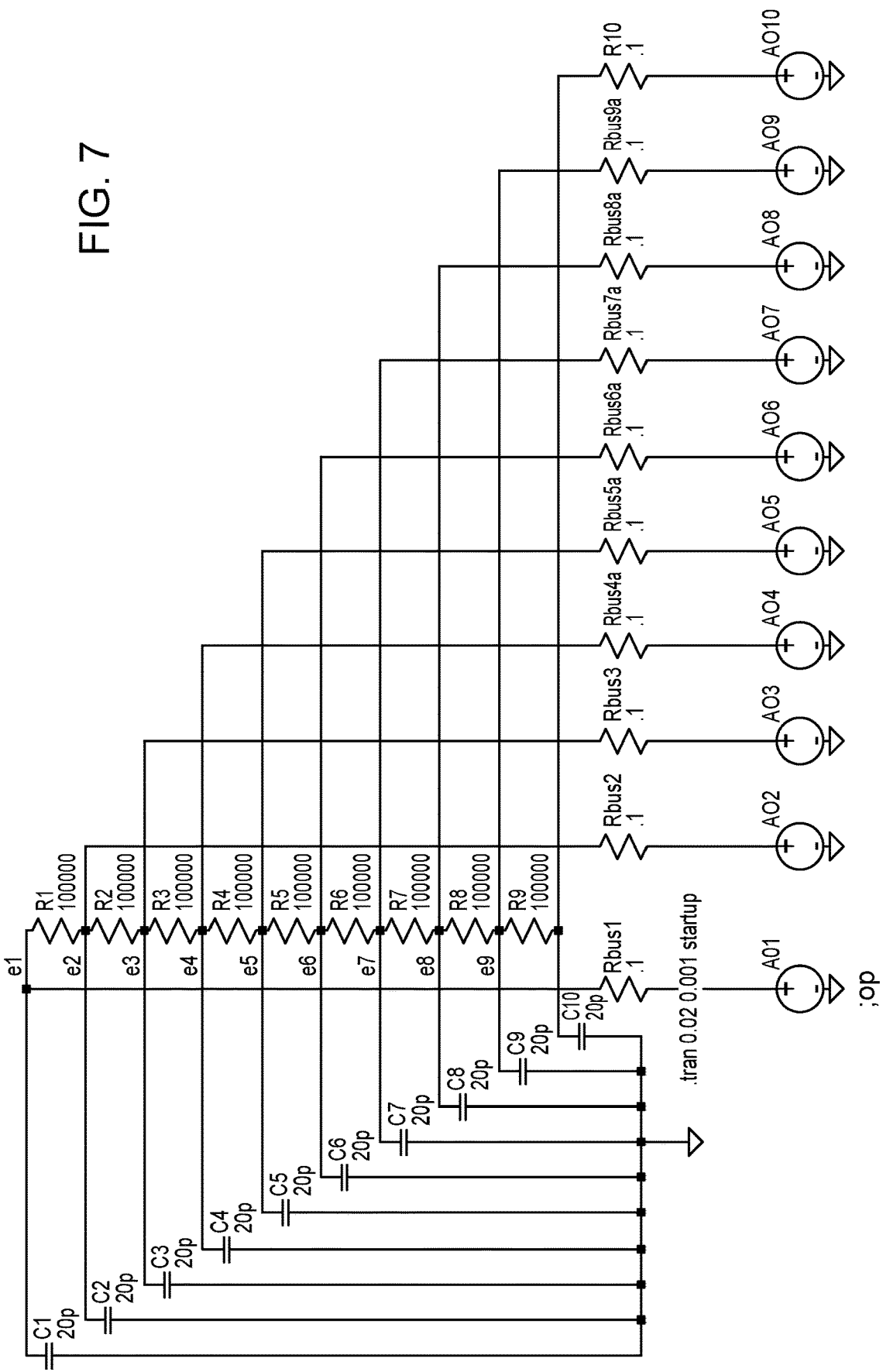
FIG. 7 shows an electro-active lens with 100 kΩ resistive bridges R1 through R9.

FIG. 7 shows an electrical schematic of an electro-active lens with in-plane resistive bridges R1 through R9 with resistance values of 100,000 ohms each. These resistive bridges are larger and thus are more likely to degrade the lens's optical performance. The increased resistance cuts the lens's current consumption, but not by enough to make the lens practical for ophthalmic applications.

Figure 8:
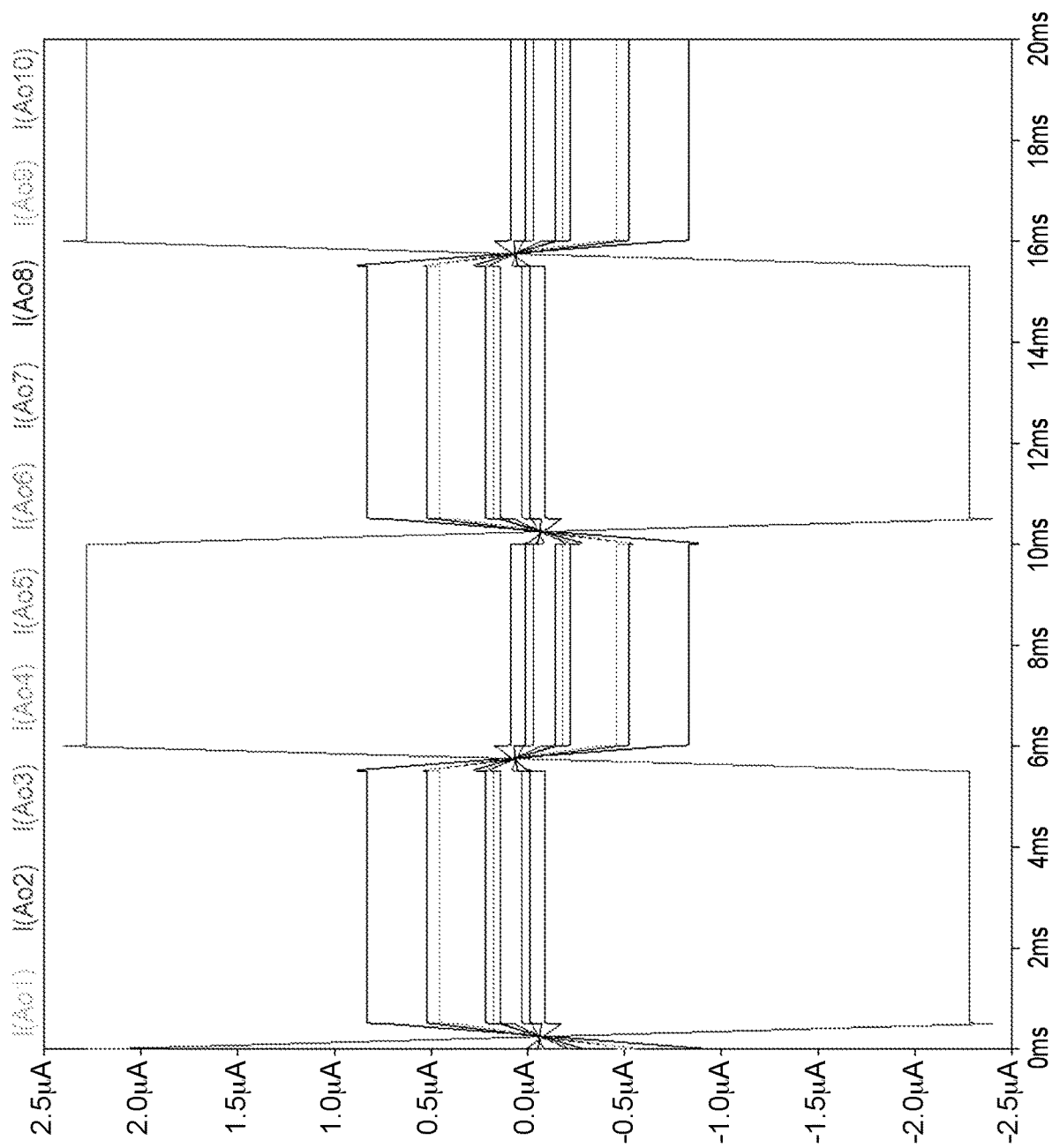
FIG. 8 shows a current flow of the electro-active lens shown in FIG. 7.

FIG. 8 shows the current flow of the lens shown in FIG. 7. Although the resistance is substantial, the peak current consumption is almost 2.5 micro-Amperes ($2.5 \times 10^{-6}$ A), which is more than twenty times higher than the current consumed by the lens without resistive bridges shown in FIG. 3. Even at this current consumption level, this electrode/resistor configuration would have a battery life that is too short for use in contact lenses or intraocular lenses.

Figure 9:
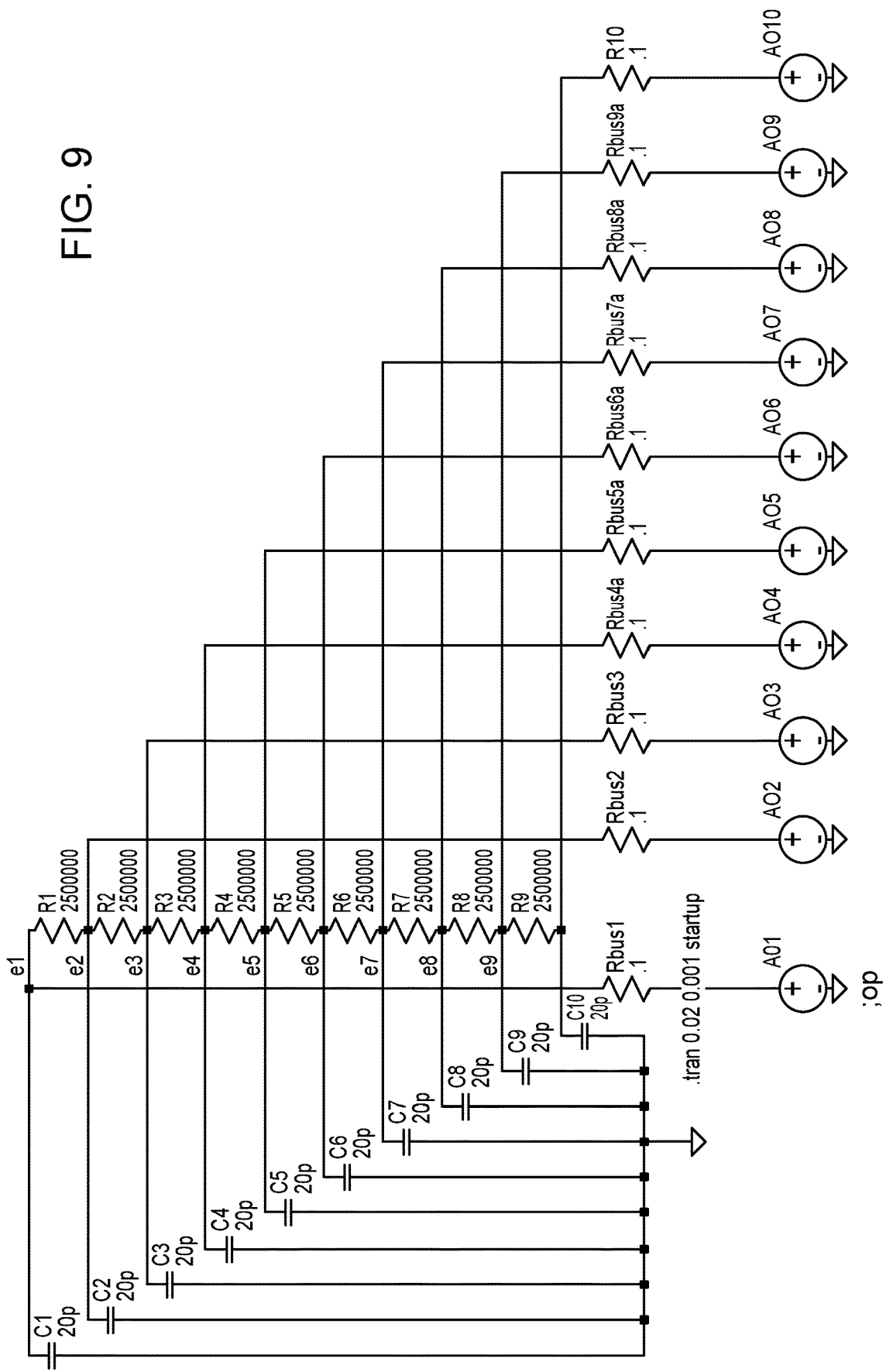
FIG. 9 shows an electro-active lens with 2.5 MΩ resistive bridges.

FIG. 9 shows an electrical schematic of an electro-active lens with the resistive bridges modified to each have 2,500,000 ohms of resistance (2.5 MΩ). These resistive bridges are about 50 microns long by 2 microns wide, which is large enough to degrade the electro-active lens's optical performance. At this resistance, the electrical current begins to approach the resistance between electrodes in an electro-active lens without resistive bridges in the circuit. But the resistive bridges are also large enough that the electrodes must be farther apart or bent or curved for the resistive bridges to fit between them. Pushing the electrodes farther apart or changing their shape degrades the lens's optical quality, making the lens unsuitable for many ophthalmic applications.

Figure 10:
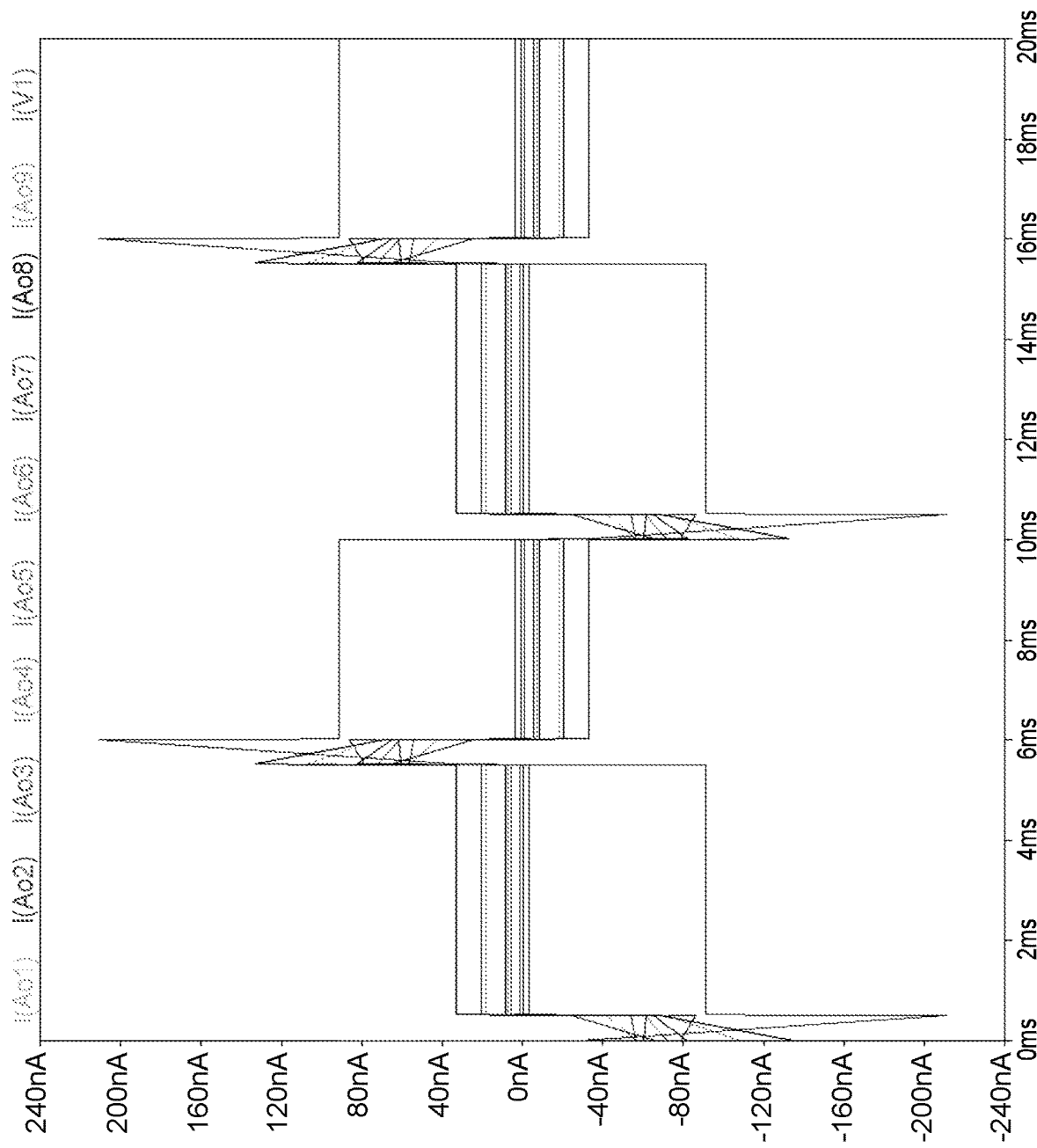
FIG. 10 shows a typical electrical current flow through each of the drive channels for the electro-active lens shown in FIG. 9.

FIG. 10 shows the typical electrical current flow through each of the drive channels for the electro-active lens described in FIG. 9. The maximum electrical current is 200 nano-Amperes ($200 \times 10^{-9}$ A), which approaches the level of power consumption of a lens without resistive bridges. The current consumption is low enough for the lens's battery life to roughly match that of an electro-active lens without resistive bridges, but the lens's optical quality is worse than that of an electro-active lens without resistive bridges. As a result, even though the lens with 2.5 MΩ in-plane resistive bridges has a battery life long enough for use as a contact lens or intraocular lens, it can't be used as a practical contact lens or intraocular lens.

Electro-Active Lenses with Raised Resistive Bridges

Figure 11:
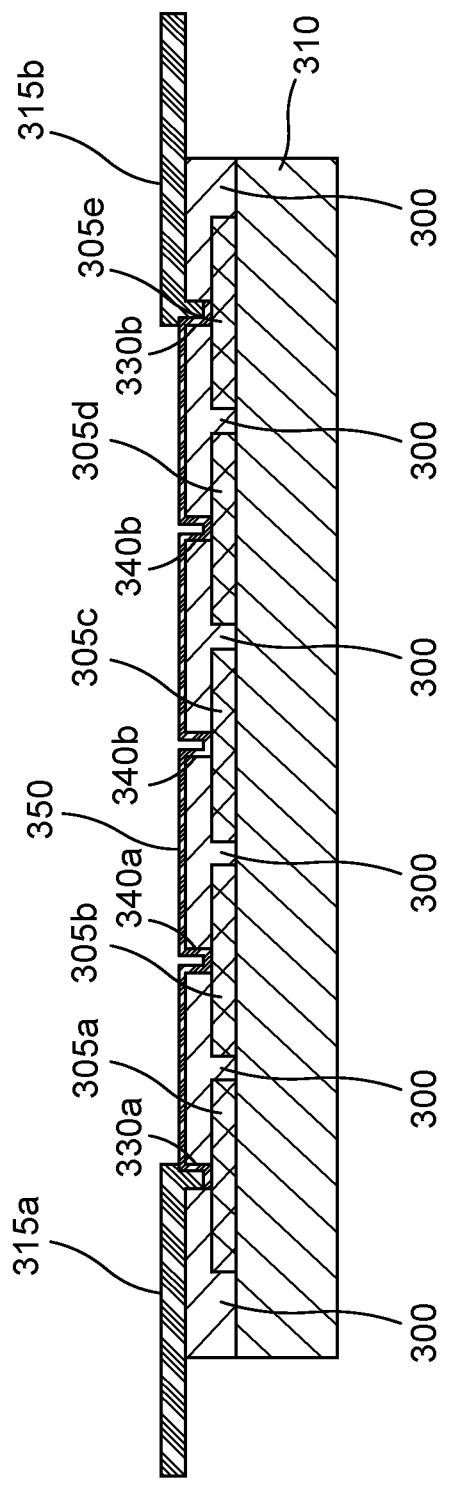
FIG. 11 shows a cross section of an electro-active lens with raised resistive bridges.

FIGS. 11-12 show electro-active lenses and concentric ring electrodes with raised resistive bridges and how they may be used in an electro-active lens. Rather than the resistors being within a gap between electrodes or connected at a break point in each electrode, there is an insulating layer between the resistor and the electrodes, which are connected through the vias in the insulating layer. This yields continuous electrode rings because there is no need to remove surface area from the electrodes to make room for the resistors. It also enables resistors with a larger ratio of length to width. This longer length-to-width ratio allows the resistors to be fabricated with a very high overall resistance and a smaller sheet resistance. For example, for a material with a sheet resistance of 100 kΩ per square, which is a common, easily fabricated type of material, the resistor between buss line connection points can have a resistance of 2.5 MΩ with a length-to-width ratio of 25:1. Other resistances and length-to-width ratios are also possible, depending on the resistive bridge material and lens design criteria, which may include desired battery life.

One other advantage of raising the resistive bridges to a level above (or below) the electrodes is that the resistive bridge material can be different than that of the electrodes. This allows the material to be selected for the electrodes that has the desired optical qualities but perhaps low resistance, and a different material selected for the resistors that has high resistance but perhaps low optical quality. Since the resistors comprise such a miniscule area of the lens, they can even be made of an opaque material without having a meaningful impact on the lens's optical quality.

FIG. 11 shows a cross section of a portion of an electro-active lens with a raised resistive bridge (resistor) 350. This resistive bridge 350 is electrically connected to several electrodes 305a-305e (collectively, electrodes 305), which are patterned onto a substrate 310. In an ophthalmic lens, such as a contact lens, there may be tens to hundreds of electrodes 305 spanning a width of about 10-20 mm, with each electrode 305 having widths on the order of microns to millimeters (e.g., 0.5 µm, 1 µm, 2 µm, 2.5 µm, 3 µm, 4 µm, 5 µm, 6 µm, 7 µm, 8 µm, 9 µm, 10 µm, 20 µm, 30 µm, 40 µm, 50 µm, 100 µm, 250 µm, 500 µm, 1 mm, 1.5 mm, 2 mm, or any other value or range up between about 0.5 µm and about 2 mm). Depending on the implementation, the electrodes 305 may of identical or different widths, possibly with a disc-shaped electrode at the center of the lens.

Unlike in an electro-active lens with conventional resistive bridges, the electrodes 305 shown in FIG. 11 are each of uniform width, with no discontinuities. In addition, the gaps between adjacent electrodes are also relatively small. For instance, these gaps may range in size from nanometers to microns (e.g., 100 nm, 200 nm, 250 nm, 300 nm, 400 nm, 500 nm, 1 µm, 2 µm, 2.5 µm, 3 µm, 4 µm, 5 µm, 6 µm, 7 µm, 8 µm, 9 µm, or 10 µm or any other value or range up to about 10 µm). The electrodes 305 may be relatively thin, e.g., less than 200 nanometers (nm), and preferably less than 40 nm.

An insulating layer 300 is blanketed over the electrodes 305, and buss line via holes 330a and 330b (collectively, buss line via holes 330) are patterned into the insulating layer 300. For instance, the insulating layer 300 may be a 120 nm thick layer of silicon dioxide or a 0.5 µm thick layer of SU-8. Resistor via holes 340a-340c (collectively, resistor via holes 340) are also patterned into the insulating layer 300. The resistive bridge 350 is then formed such that the underlying electrodes 305 are connected through the resistive bridge 350 through the via holes 330 and 340. Buss lines 315a and 315b (collectively, buss lines 315) connect through the via holes 330a and 330b, respectively, to both the resistive bridge 350 and the electrodes 305a and 305e. Electrodes 305a and 305e are powered directly by buss lines 315a and 315b, while electrodes 305b-305d are powered indirectly through the resistive bridge 350.

The sheet resistance of the resistive bridge 350 may range of from approximately 0.1 MΩ per square to approximately 100 MΩ per square or more. The sheet resistance of the insulating layer 300 is greater than approximately $10^{18}$ Ω per meter, and ideally infinite. The resistance of the electrodes 305 is less than approximately 200 Ω per square. Other measures of resistance may be used depending on the optical effects sought to be achieved. The resistive layer may be relatively thin, e.g., less than 200 nanometers (nm), and preferably less than 40 nm.

Although FIG. 11 shows the buss lines 315 connecting to resistive bridge 350 inside of buss line via holes 330 in such a manner as sharing the electrode 305, other configurations can be made by those skilled in the art of via hole design. For example, the resistive bridge could occupy the entire bottom of the via hole with the buss line on top of the resistive bridge material. The buss line could also occupy the entire bottom of the via hole with the resistive bridge on top of the buss line material. Likewise, the resistive bridge could be connected to more or fewer electrodes.

Having the resistive bridge 350 above the insulating layer 300 provides more room for resistor construction, allowing higher length-to-width ratios to be used without compromising or interrupting the integrity of the electrodes 305. All other things being equal, increasing a resistor's length-to-width ratio increases its resistance. And higher resistance translates to lower current consumption and longer battery life. A higher length-to-width ratio might not be possible if the resistor had to remain within the gap between the electrodes at the plane of the electrodes.

Placing the resistive bridge 350 above the insulating layer 300 and electrodes also provides for greater flexibility in material choices for the resistor's construction and more robust, more forgiving error tolerance when constructing resistors with high resistance. For instance, the resistive bridge 350 can made of a transparent conductive material, such as indium tin oxide, or a layer of material that is thin enough to be translucent, such as a layer of nickel that is microns thick. If the resistive bridge 350 is used in a reflection geometry, or if the resistive bridge 350 is relatively small, it can be made of an opaque material (e.g., a thicker layer of metal).

Figure 12A:
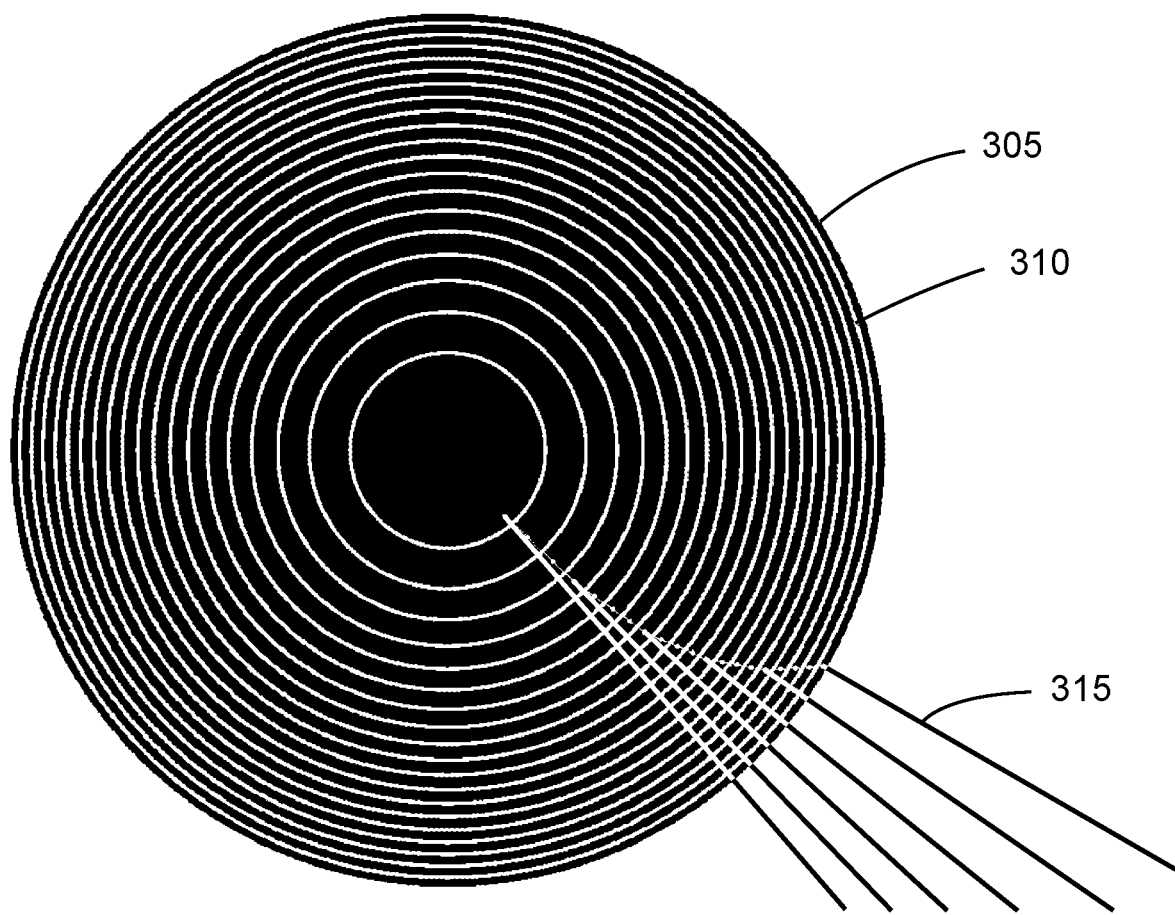
Figure 12B:
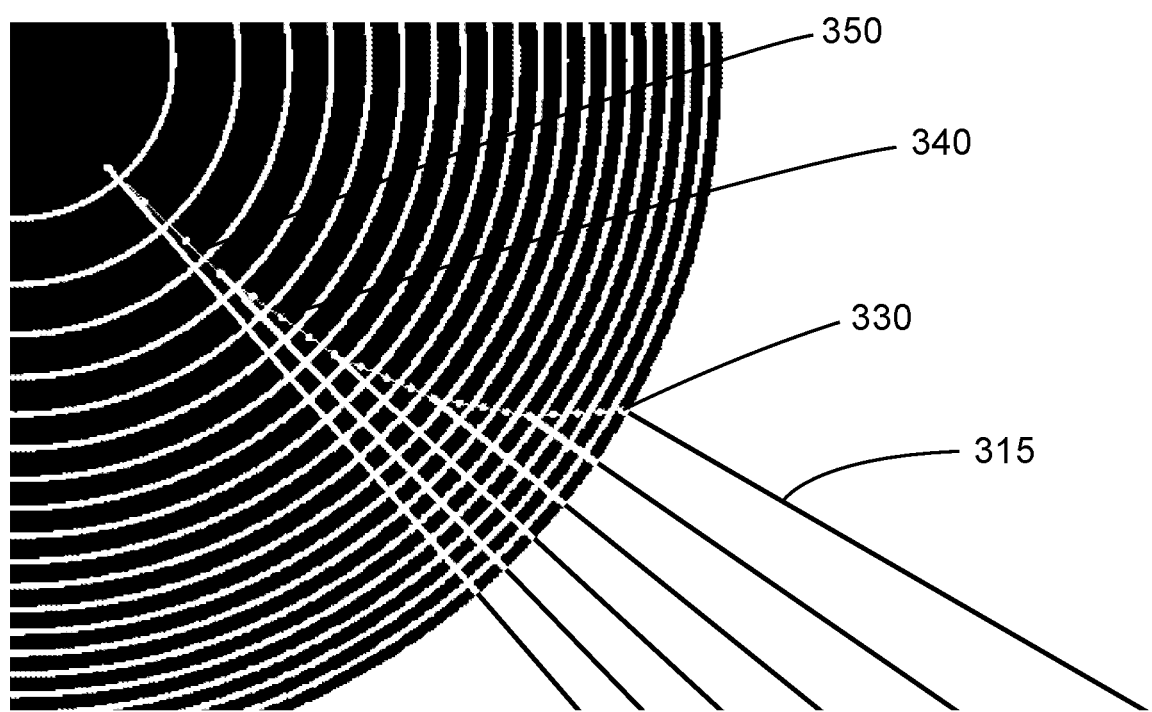

FIGS. 12A and 12B show a plan view of the electrodes 305, buss lines 315, buss line via holes 330, resistor via holes 340, and resistive bridge 350. (FIG. 12B is a close-up view.) Buss lines 315 (six are shown) penetrate the insulation layer at buss line via holes 315 in six locations, making electrical connection to the electrodes 305. A resistive bridge 350 is also connected at buss line via holes 315. The resistive bridge 350 connects to the unpowered electrodes 305 through resistor-only via holes 340 (fourteen are shown).

FIG. 12C shows the buss lines 315, buss line via holes 330, resistor via holes 340, and resistive bridge 350 without the electrodes 305. Although the resistive bridge 350 is shown as set of straight line segments (each of which could be considered as an individual resistive bridge), they could be other shapes and sizes as well to provide better control of the desired resistance.

For example, FIG. 12D shows a raised resistive bridge 350' with curved bridge segments 352a-352d (collectively, curved bridge segments 352) that connect adjacent via holes 330 and 340. In this case, the curved bridge segments 352 form an undulating or sine-like path between a pair of buss line via holes 330. In other cases, the resistive bridge segments could take a different non-straight (e.g., curved, twisted, or jagged) path from one via hole to the next. Moreover, each bridge segment can have a different curvature or path—some can have larger radii of curvature than others or take paths of different shapes. This would increase the length and resistance of each segment and of the resistive bridge as a whole. The curvature may also affect the resistive bridge's other electrical properties, including its inductance, capacitance, or both.

Figure 12E:
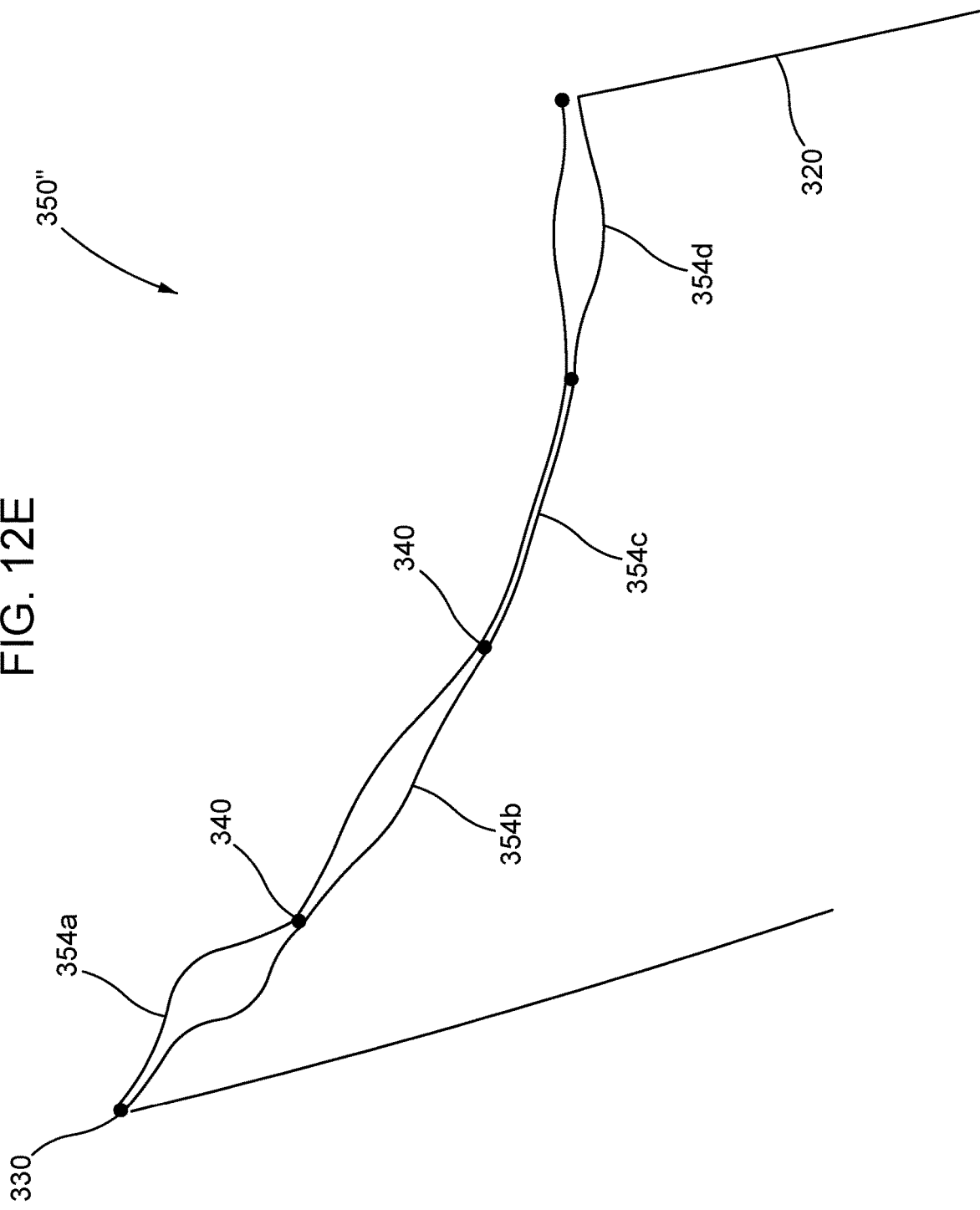
FIG. 12E shows a raised resistive bridge with bridge segments having variable widths.

Similarly, FIG. 12E shows a raised resistive bridge 350" with segments 354a-354d (collectively, variable-width bridge segments 354) whose widths vary from segment to segment. In this case, the segments 354 bulge in the middle, but other shapes could be used as well. This variation may be used to provide resistors to compensate for variations in resistance due to length variations among segments of the resistive bridge. The width of each segment may also be varied deliberately to create non-uniform resistance values from segment to segment. For instance, the segment width may be varied to create a non-linear resistance gradient, such as a parabolic resistance gradient. This parabolic resistance gradient could be used to create a parabolic gradient of the electric field resulting in a lens with even fewer buss lines (and better optical quality).

An Electro-Active Contact Lens with Raised Resistive Bridges

Figure 13:
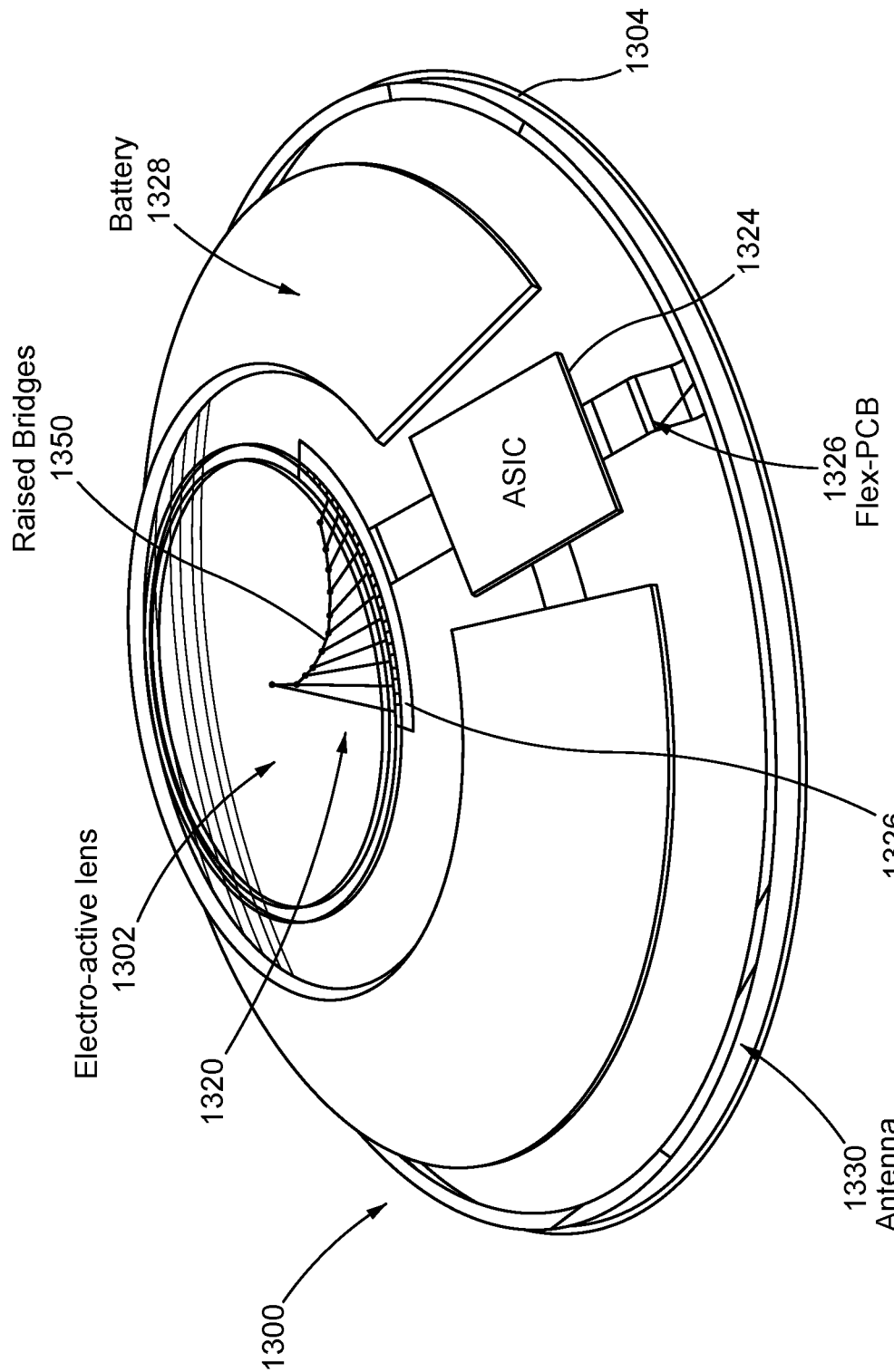
FIG. 13 shows an electro-active contact lens with raised resistive bridges.

FIG. 13 shows an electro-active contact lens 1300 with raised resistive bridges 1350. The electro-active contact lens 1300 includes an electro-active lens element 1302 with an electro-active material, such as nematic or cholesteric liquid crystal, sandwiched between a pair of transparent substrates, just like the lens 100 shown in FIG. 1. The liquid crystal could also be contained within a cavity defined by folding a single substrate onto itself. One of the surfaces opposite the liquid crystal material is patterned to include a plurality of concentric ring electrodes made of transparent conductive material as shown in FIGS. 11 and 12A.

The electro-active lens element 1302 also includes a raised resistive bridge 1350 disposed on an insulating layer as shown in FIG. 11. This raised resistive bridge 1350 includes segments that connect the electrodes to each other and to buss lines 1320, also as shown in FIGS. 11 and 12A. The buss lines 1320 connect in turn to a bus 1322, which connects to a processor (here, an ASIC 1324) via a flexible printed circuit board (PCB) 1326. The flexible PCB 1326 also connects the ASIC 1324 to a ring-shaped power battery 1328 and a ring-shaped antenna 1330, both of which are concentric with the electro-active lens element 1302 as shown in FIG. 13. All of these components are completely or partially embedded in a base optical element 1304. This base optical element 1304 may provide additional optical power—i.e., it may function as a fixed lens—and can be formed of any suitable material, include soft hydrogels like those used in soft contact lenses.

In operation, the ASIC 1324 actuates the electro-active lens element 1302 in response to signals received by the antenna 1330 or generated by one or more sensors (not shown) embedded in the electro-active contact lens 1300. The ASIC 1324 controls the optical power provided by the electro-active lens element 1302 by modulating the voltages applied to the electrodes via the buss 1326, buss lines 1320, and raised resistive bridges 1350. Because the raised resistive bridges 1350 are in a different plane than the electrodes, they can be relatively large (e.g., 2.5 MΩ) without degrading the lens's optical performance. At this size, they also limit current consumption to reasonable rates (e.g., on the order of 100-200 nA), which makes it possible for the battery 1328 to go long stretches (e.g., 40 hours or more) between rechargings (e.g., via the coil-shaped antenna 1330) or before the electro-active contact lens 1300 is thrown away.

Making an Electro-Active Intraocular Lens with Raised Resistive Bridges

Figure 14:
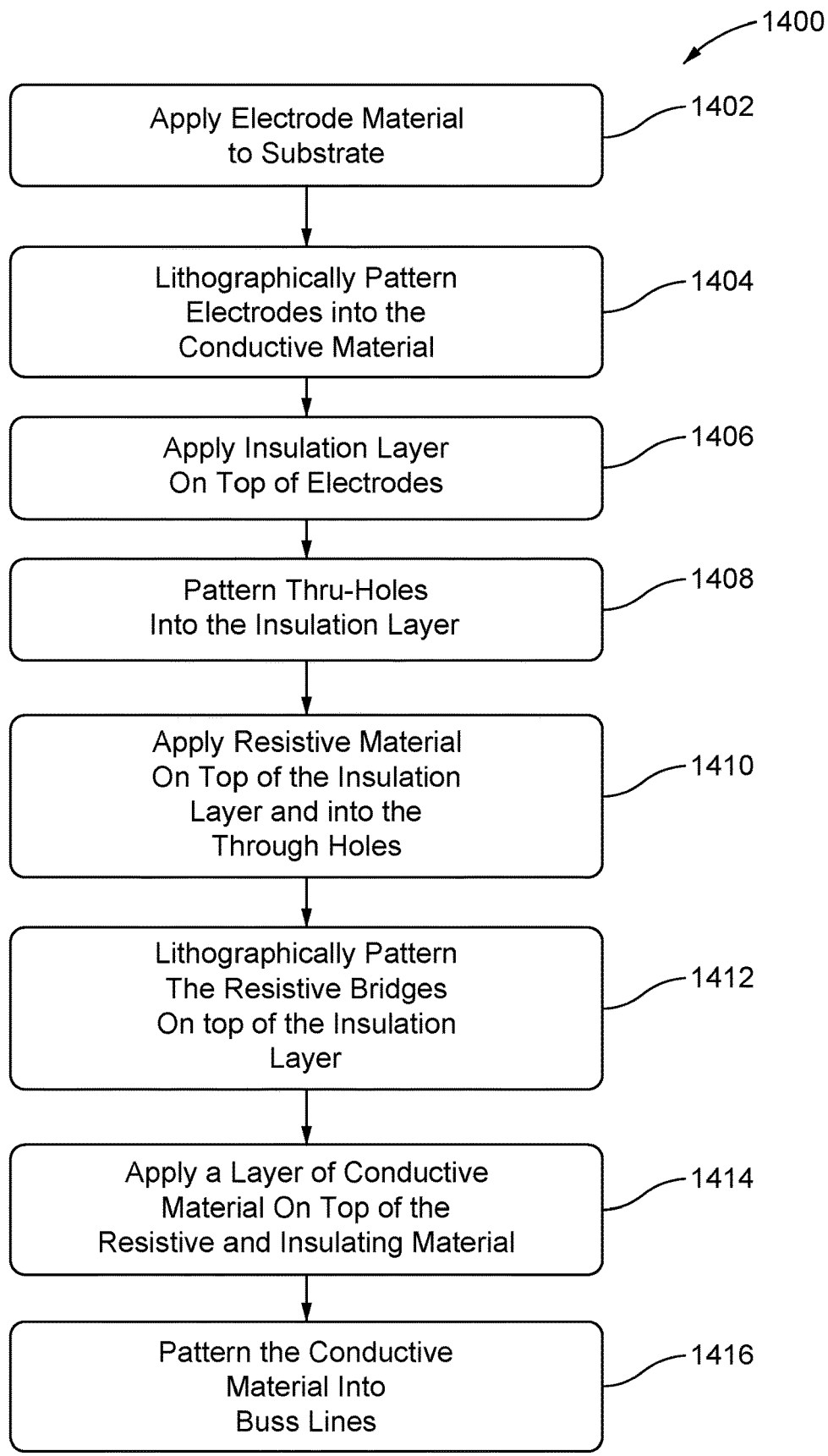
FIG. 14 shows a process for making an electro-active lens with resistive bridges disposed on an insulating layer above an electrode layer.

FIG. 14 shows a process 1400 for making an electro-active intraocular lens with raised resistive bridges. In step 1402, conductive material (e.g., ITO) is deposited on a transparent substrate, such as a piece of flexible polymer. The electrode material is lithographically pattern to form electrodes (e.g., concentric ring-shaped electrodes) in step 1404. Next, in step 1406, a layer of insulating material, such as silicon dioxide, is deposited on the patterned electrodes. Through-holes are lithographically patterned into the insulating layer in step 1408. In step 1410, resistive material is disposed on the insulating layer and in the through-holes, forming electrical connections to the electrodes. Suitable resistive materials include, but are not limited to, alloys of nickel and chromium, ITO doped with oxygen, combinations of metals with oxides, and resistive polymers, such as poly(3,4-ethylenedioxythiophene) poly(styrenesulfonate) (PEDOT:PSS). The resistive material is patterned lithographically to form raised resistive bridges in step 1412, A layer of conductive material is disposed on the resistive bridges and exposed insulating layer in step 1414 and patterned to form the buss lines in step 1416.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the technology disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An electro-optic lens comprising:
a first substantially transparent substrate;
a plurality of electrodes disposed on a surface of the first substantially transparent substrate, the plurality of electrodes comprising a first electrode disposed on the surface of the first substantially transparent substrate and a second electrode disposed on the surface of the first substantially transparent substrate;
an insulating layer disposed on the first electrode, the second electrode, and on a portion of the surface of the first substantially transparent substrate between the first electrode and the second electrode; and
a resistive bridge disposed on the insulating layer over the portion of the surface of the first substantially transparent substrate between the first electrode and the second electrode, the resistive bridge connecting the first electrode with the second electrode via holes patterned into the insulating layer.

2. The electro-optic lens of claim 1, wherein the plurality of electrodes comprises a plurality of concentric ring electrodes, the first electrode is a first concentric ring electrode, and the second electrode is a second concentric ring electrode.

3. The electro-optic lens of claim 2, wherein the first concentric ring electrode has a constant width.

4. The electro-optic lens of claim 1, wherein the plurality of electrodes is formed of a first material having a first sheet resistance and the resistive bridge is formed of a second material having a second sheet resistance higher than the first sheet resistance.

5. The electro-optic lens of claim 1, wherein the insulating layer on the surface of the first substantially transparent substrate comprises:
insulating material disposed between the first electrode and the second electrode, the insulating layer spanning a gap between the first electrode and the second electrode of less than about 3 microns.

6. The electro-optic lens of claim 1, wherein the resistive bridge has a resistance of at least about 2.5 MΩ.

7. The electro-optic lens of claim 1, wherein the resistive bridge has a length-to-width ratio of about 25:1.

8. The electro-optic lens of claim 1, wherein the resistive bridge comprises at least one of nickel, chromium, indium tin oxide, or resistive polymer.

9. The electro-optic lens of claim 1, wherein the resistive bridge comprises a plurality of resistive segments, each resistive segment in the plurality of resistive segments being in electrical communication with a corresponding pair of electrodes in the plurality of electrodes.

10. The electro-optic lens of claim 9, wherein the plurality of resistive segments includes a first resistive segment with a first width and a second resistive segment with a second width greater than the first width.

11. The electro-optic lens of claim 9, wherein the plurality of resistive segments includes a first resistive segment with a first length and a second resistive segment with a second length greater than the first length.

12. The electro-optic lens of claim 9, wherein at least one resistive segment in the plurality of resistive segments has at least one of a curved edge or bent edge.

13. The electro-optic lens of claim 9, wherein each resistive segment in the plurality of resistive segments has a different resistance.

14. The electro-optic lens of claim 9, wherein the plurality of resistive segments provides a non-linear resistance gradient.

15. The electro-optic lens of claim 14, wherein the non-linear resistance gradient is a parabolic resistance gradient.

16. The electro-optic lens of claim 1, wherein the resistive bridge is configured to limit current consumption by the electro-optic lens to about 100-200 nA.

17. The electro-optic lens of claim 1, further comprising:
an input connection, connected to the first electrode, and an output connection, connected to another electrode in the plurality of electrodes, to power the first electrode directly and to power the second electrode via the resistive bridge.

18. The electro-optic lens of claim 1, wherein the first electrode and the second electrode are disposed directly on the surface of the first substantially transparent substrate.

19. A method of operating an electro-optic lens comprising a plurality of electrodes, the plurality of electrodes comprising a first electrode disposed on a surface of a substrate and a second electrode disposed on the surface of the substrate, the method comprising:
applying voltage to the first electrode via a buss line connected to the first electrode via a first hole in an insulating layer disposed on the plurality of electrodes; and
applying voltage from the buss line to the second electrode via the first electrode and a resistive bridge spanning a portion of the insulating layer on the surface of the substrate between the first electrode and the second electrode.

20. The method of claim 19, wherein the resistive bridge limits current consumption by the electro-optic lens to about 100-200 nA.

21. A method of making an electro-optic lens, the method comprising:
forming a plurality of electrodes on a substrate, the plurality of electrodes comprising a first electrode and a second electrode on a surface of the substrate;
depositing a layer of insulating material on the plurality of electrodes and on a portion of the surface of the substrate between the first electrode and the second electrode;
forming a plurality of through holes in the layer of insulating material, the plurality of through holes comprising a first through hole connecting to the first electrode and a second through connecting to the second electrode;
depositing a resistive material on the layer of insulating material over the portion of the surface of the substrate between the first electrode and the second electrode and in the plurality of through holes; and patterning the resistive material to form a plurality of resistors, the plurality of resistors comprising a first resistor connecting the first electrode to the second electrode and disposed on the insulating material extending over the portion of the surface of the substrate between the first electrode and the second electrode.

22. The method of claim 21, wherein forming the plurality of electrodes comprises forming a plurality of concentric ring electrodes.

23. The method of claim 22, wherein forming the plurality of concentric ring electrodes comprises forming a first concentric ring electrode separated from a second concentric ring electrode by a gap of less than about 3 microns.

24. The method of claim 22, wherein forming the plurality of concentric ring electrodes comprises forming a concentric ring electrode having a constant width.

25. The method of claim 21, wherein depositing the resistive material comprises depositing material having a sheet resistance higher than a sheet resistance of the plurality of electrodes.

26. The method of claim 21, wherein patterning the resistive material to form the plurality of resistors comprises forming at least one resistor having a resistance of at least about 2.5 MΩ.

27. The method of claim 21, wherein patterning the resistive material to form the plurality of resistors comprises forming at least one resistor having a length-to-width ratio of about 25:1.

28. The method of claim 21, wherein patterning the resistive material to form the plurality of resistors comprises forming a first resistor with a first width and a second resistor segment with a second width greater than the first width.

29. The method of claim 21, wherein patterning the resistive material to form the plurality of resistors comprises forming a first resistor with a first length and a second resistor with a second length greater than the first length.

30. The method of claim 21, wherein patterning the resistive material to form the plurality of resistors comprises forming at least one resistor with a curved edge.

31. The method of claim 21, further comprising:
forming a buss line connected to at least one electrode in the plurality of electrodes.

32. The method of claim 21, wherein the plurality of resistors has a resistivity of less than 200 Ω per square, the insulating material has a resistivity of at least $10^{18}$ Ω per meter, the resistive material has a resistivity of at least 0.1 MΩ/square.

33. An electro-active contact lens comprising:
a base optical element;
an electro-active element embedded within the base optical element, the electro-active element comprising:
a plurality of electrodes comprising a first electrode and a second electrode on a surface of a substrate;
an insulating layer disposed on the plurality of electrodes and on a portion of the surface of the substrate between the first electrode and the second electrode; and
a resistive bridge disposed on the insulating layer on the portion of the surface of the substrate between the first electrode and the second electrode, the resistive bridge connecting the first electrode in the plurality of electrodes with the second electrode in the plurality of electrodes via holes patterned into the insulating layer.

34. The electro-active contact lens of claim 33, wherein the resistive bridge has a resistance of at least about 2.5 MΩ.

* * * * *